(12) United States Patent
Hoffa et al.

(10) Patent No.: US 8,858,464 B2
(45) Date of Patent: *Oct. 14, 2014

(54) SURGICAL SYSTEM

(71) Applicant: Suros Surgical Systems, Inc., Indianapolis, IN (US)

(72) Inventors: Michael Hoffa, Brownsburg, IN (US); Michael E. Miller, Trafalgar, IN (US); Joseph L. Mark, Indianapolis, IN (US); Jacob Flagle, New Palestine, IN (US); Justin Smith, Indianapolis, IN (US); Jason M. Butcher, Lafayette, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,286

(22) Filed: Aug. 15, 2013

(65) Prior Publication Data

US 2013/0331732 A1  Dec. 12, 2013

Related U.S. Application Data

(63) Continuation of application No. 12/496,316, filed on Jul. 1, 2009, now Pat. No. 8,529,468.

(51) Int. Cl.
*A61B 10/02* (2006.01)
*A61B 10/00* (2006.01)
*A61B 19/00* (2006.01)
*A61B 17/00* (2006.01)

(52) U.S. Cl.
CPC ..... *A61B 10/0283* (2013.01); *A61B 2010/0093* (2013.01); *A61B 2019/464* (2013.01); *A61B 2010/0208* (2013.01); *A61B 2017/00477* (2013.01); *A61B 10/0275* (2013.01); *A61B 2010/0225* (2013.01)

USPC .......................................... 600/566; 600/565

(58) Field of Classification Search
USPC ........... 600/562, 564–568; 606/167, 170, 171
See application file for complete search history.

(56) References Cited

U.S. PATENT DOCUMENTS

| 1,337,733 A | 4/1920 | Sweetland et al. |
| 1,693,741 A | 12/1928 | Wuest |

(Continued)

FOREIGN PATENT DOCUMENTS

| DE | 9112550 | 11/1991 |
| EP | 0541970 | 5/1993 |

(Continued)

OTHER PUBLICATIONS

Office Action for U.S. Appl. No. 10/958,026 dated Jan. 10, 2005 (9 pages).

(Continued)

*Primary Examiner* — Rene Towa
*Assistant Examiner* — Emily Lloyd
(74) *Attorney, Agent, or Firm* — Vista IP Law Group LLP

(57) ABSTRACT

A surgical device is disclosed that comprises a cutting element, a biopsy line, a motor line, and a vacuum line. The cutting element includes an outer cannula and an inner cannula. The biopsy line is operatively connected to a control console for moving the inner cannula within the outer cannula to cut tissue cores. The motor line is operatively connected to the control console for operating the surgical device. The vacuum line is operatively connected to the inner cannula. A selectively openable tissue filter is operatively connected to the inner cannula, and is also connected to the vacuum line.

12 Claims, 16 Drawing Sheets

(56) References Cited

U.S. PATENT DOCUMENTS

| | | |
|---|---|---|
| 1,734,652 A | 11/1929 | Sweetland |
| 1,941,982 A | 1/1934 | Gill |
| 2,047,714 A | 7/1936 | Smith |
| 2,656,930 A | 10/1953 | De Vries |
| 2,689,048 A | 9/1954 | Powers |
| 3,401,684 A | 9/1968 | Dremann |
| 3,456,806 A | 7/1969 | Borston |
| 3,561,429 A | 2/1971 | Jewett et al. |
| 3,606,878 A | 9/1971 | Kellogg |
| 3,785,380 A | 1/1974 | Brumfield |
| 3,815,604 A | 6/1974 | O'Malley et al. |
| 3,833,000 A | 9/1974 | Bridgman |
| 3,889,657 A | 6/1975 | Baumgarten |
| 3,890,712 A | 6/1975 | Lopez |
| 3,937,222 A | 2/1976 | Banko |
| 3,938,505 A | 2/1976 | Jamshidi |
| 3,945,375 A | 3/1976 | Banko |
| 3,994,297 A | 11/1976 | Kopf |
| 4,007,742 A | 2/1977 | Banko |
| D243,559 S | 3/1977 | Hoyle et al. |
| 4,019,514 A | 4/1977 | Banko |
| 4,083,706 A | 4/1978 | Wiley |
| 4,101,756 A | 7/1978 | Yamano |
| 4,117,843 A | 10/1978 | Banko |
| 4,159,773 A | 7/1979 | Losenno |
| 4,167,943 A | 9/1979 | Banko |
| 4,167,944 A | 9/1979 | Banko |
| 4,177,814 A | 12/1979 | Knepshield et al. |
| 4,210,146 A | 7/1980 | Banko |
| 4,220,252 A | 9/1980 | Beall et al. |
| 4,221,225 A | 9/1980 | Sloan et al. |
| 4,257,425 A | 3/1981 | Ryan |
| 4,282,098 A | 8/1981 | Morgan, Jr. |
| 4,308,878 A | 1/1982 | Silva |
| 4,316,465 A | 2/1982 | Dotson, Jr. |
| 4,354,093 A | 10/1982 | Zago |
| 4,368,734 A | 1/1983 | Banko |
| 4,382,808 A | 5/1983 | Van Wormer, Jr. et al. |
| 4,468,217 A | 8/1984 | Kuzmick et al. |
| 4,513,745 A | 4/1985 | Amoils |
| 4,530,356 A | 7/1985 | Helfgott et al. |
| 4,533,818 A | 8/1985 | Green |
| 4,549,554 A | 10/1985 | Markham |
| 4,562,838 A | 1/1986 | Walker |
| 4,644,951 A | 2/1987 | Bays |
| 4,651,753 A | 3/1987 | Lifton |
| 4,662,869 A | 5/1987 | Wright |
| 4,696,298 A | 9/1987 | Higgins et al. |
| 4,708,147 A | 11/1987 | Haaga |
| 4,803,341 A | 2/1989 | Barowski et al. |
| 4,817,631 A | 4/1989 | Schnepp-Pesch et al. |
| 4,850,373 A | 7/1989 | Zatloukal et al. |
| 4,871,074 A | 10/1989 | Bryson et al. |
| 4,886,492 A | 12/1989 | Brooke et al. |
| 4,893,635 A | 1/1990 | De Groot et al. |
| 4,919,146 A | 4/1990 | Rhinehart et al. |
| 4,926,877 A | 5/1990 | Bookwalter |
| RE33,258 E | 7/1990 | Onik et al. |
| 4,973,019 A | 11/1990 | Baird et al. |
| 4,985,027 A | 1/1991 | Dressel |
| 4,989,614 A | 2/1991 | Dejter, Jr. et al. |
| 5,027,827 A | 7/1991 | Cody et al. |
| 5,031,778 A | 7/1991 | Edgecombe |
| 5,052,999 A | 10/1991 | Klein |
| 5,054,615 A | 10/1991 | Stillwagon et al. |
| 5,074,311 A | 12/1991 | Hasson |
| 5,080,869 A | 1/1992 | McCormick |
| 5,090,649 A | 2/1992 | Tipp |
| 5,108,381 A | 4/1992 | Kolozsi |
| 5,124,532 A | 6/1992 | Hafey et al. |
| 5,141,189 A | 8/1992 | Andrew |
| D329,304 S | 9/1992 | Tipp |
| 5,172,701 A | 12/1992 | Leight |
| D332,670 S | 1/1993 | McFarland |
| 5,176,677 A | 1/1993 | Wuchinich |
| 5,183,052 A | 2/1993 | Terwilliger |
| 5,192,439 A | 3/1993 | Roth et al. |
| 5,197,968 A | 3/1993 | Clement |
| 5,213,110 A | 5/1993 | Kedem et al. |
| 5,243,994 A | 9/1993 | Ranalletta |
| D342,585 S | 12/1993 | Fischbach et al. |
| 5,275,609 A | 1/1994 | Pingleton et al. |
| 5,284,156 A | 2/1994 | Schramm et al. |
| 5,285,795 A | 2/1994 | Ryan et al. |
| 5,295,980 A | 3/1994 | Ersek |
| 5,348,022 A | 9/1994 | Leight et al. |
| 5,358,638 A | 10/1994 | Gershenson |
| 5,403,276 A | 4/1995 | Schechter et al. |
| 5,411,513 A | 5/1995 | Ireland et al. |
| 5,423,844 A | 6/1995 | Miller |
| 5,429,138 A | 7/1995 | Jamshidi |
| 5,429,596 A | 7/1995 | Arias et al. |
| 5,456,267 A | 10/1995 | Stark |
| 5,458,112 A | 10/1995 | Weaver |
| 5,464,300 A | 11/1995 | Crainich |
| 5,505,210 A | 4/1996 | Clement |
| 5,520,635 A | 5/1996 | Gelbfish |
| 5,520,801 A | 5/1996 | Gerber et al. |
| D371,220 S | 6/1996 | Behrens |
| 5,526,822 A | 6/1996 | Burbank et al. |
| 5,533,642 A | 7/1996 | Lafond et al. |
| 5,543,114 A | 8/1996 | Dudek |
| 5,575,293 A | 11/1996 | Miller et al. |
| 5,580,347 A | 12/1996 | Reimels |
| D377,996 S | 2/1997 | Gilbert |
| 5,615,782 A | 4/1997 | Choe |
| D379,554 S | 5/1997 | Landers |
| 5,630,939 A | 5/1997 | Bulard et al. |
| 5,643,304 A | 7/1997 | Schechter et al. |
| 5,649,547 A | 7/1997 | Ritchart et al. |
| 5,669,876 A | 9/1997 | Schechter et al. |
| 5,669,923 A | 9/1997 | Gordon |
| D386,818 S | 11/1997 | Boomfield |
| 5,685,838 A | 11/1997 | Peters et al. |
| 5,685,840 A | 11/1997 | Schechter et al. |
| 5,730,717 A | 3/1998 | Gelbfish |
| 5,769,086 A | 6/1998 | Ritchart et al. |
| 5,775,333 A | 7/1998 | Burbank et al. |
| 5,779,649 A | 7/1998 | Herbert |
| 5,782,849 A | 7/1998 | Miller |
| 5,788,651 A | 8/1998 | Weilandt |
| 5,794,626 A | 8/1998 | Kieturakis |
| 5,794,799 A | 8/1998 | Collins et al. |
| 5,807,275 A | 9/1998 | Jamshidi |
| 5,810,806 A | 9/1998 | Ritchart et al. |
| 5,843,111 A | 12/1998 | Vijfvinkel |
| 5,848,978 A | 12/1998 | Cecchi |
| D403,810 S | 1/1999 | Owens |
| 5,893,862 A | 4/1999 | Pratt et al. |
| 5,911,701 A | 6/1999 | Miller et al. |
| 5,913,857 A | 6/1999 | Ritchart et al. |
| 5,916,229 A | 6/1999 | Evans |
| 5,928,164 A | 7/1999 | Burbank et al. |
| 5,928,218 A | 7/1999 | Gelbfish |
| 5,944,673 A | 8/1999 | Gregoire et al. |
| 5,964,716 A | 10/1999 | Gregoire et al. |
| 5,971,939 A | 10/1999 | DeSantis et al. |
| 5,980,469 A | 11/1999 | Burbank et al. |
| 5,980,545 A | 11/1999 | Pacala et al. |
| 5,980,546 A | 11/1999 | Hood |
| 5,997,560 A | 12/1999 | Miller |
| 6,007,497 A | 12/1999 | Huitema |
| 6,017,316 A | 1/2000 | Ritchart et al. |
| 6,019,733 A | 2/2000 | Farascioni |
| 6,022,324 A | 2/2000 | Skinner |
| 6,022,326 A | 2/2000 | Tatum et al. |
| D423,717 S | 4/2000 | Taylor |
| 6,050,955 A | 4/2000 | Bryan et al. |
| D426,025 S | 5/2000 | Holmes et al. |
| 6,077,230 A | 6/2000 | Gregoire et al. |
| 6,080,113 A | 6/2000 | Heneveld et al. |
| 6,085,749 A | 7/2000 | Wardle et al. |
| 6,086,544 A | 7/2000 | Hibner et al. |
| 6,096,042 A | 8/2000 | Herbert |

(56) References Cited

U.S. PATENT DOCUMENTS

| | | |
|---|---|---|
| 6,109,446 A | 8/2000 | Foote |
| 6,120,462 A | 9/2000 | Hibner et al. |
| 6,120,463 A | 9/2000 | Bauer |
| 6,123,299 A | 9/2000 | Zach, Sr. |
| 6,139,738 A | 10/2000 | Maxwell |
| 6,142,955 A | 11/2000 | Farascioni et al. |
| 6,148,857 A | 11/2000 | West et al. |
| 6,162,187 A | 12/2000 | Buzzard et al. |
| 6,193,414 B1 | 2/2001 | Balzano |
| 6,193,673 B1 | 2/2001 | Viola et al. |
| 6,261,302 B1 | 7/2001 | Voegele et al. |
| 6,273,862 B1 | 8/2001 | Privitera et al. |
| 6,293,957 B1 | 9/2001 | Peters et al. |
| 6,331,165 B1 | 12/2001 | Turturro et al. |
| 6,346,107 B1 | 2/2002 | Cucin |
| 6,379,372 B1 | 4/2002 | Dehdashtian et al. |
| 6,402,701 B1 | 6/2002 | Kaplan et al. |
| 6,428,487 B1 | 8/2002 | Burdorff et al. |
| 6,461,350 B1 | 10/2002 | Underwood et al. |
| 6,468,225 B1 | 10/2002 | Lundgren |
| 6,468,227 B2 | 10/2002 | Zimmon |
| 6,471,700 B1 | 10/2002 | Burbank et al. |
| 6,485,436 B1 | 11/2002 | Truckai et al. |
| 6,592,508 B1 | 7/2003 | Ravins et al. |
| 6,632,182 B1 | 10/2003 | Treat |
| 6,638,235 B2 | 10/2003 | Miller et al. |
| 6,743,245 B2 | 6/2004 | Lobdell |
| 6,752,768 B2 | 6/2004 | Burdorff et al. |
| 6,758,824 B1 | 7/2004 | Miller et al. |
| 6,951,611 B2 | 10/2005 | Dannenmaier et al. |
| 7,041,217 B1 | 5/2006 | Close et al. |
| 7,226,424 B2 | 6/2007 | Ritchart et al. |
| 7,316,726 B2 | 1/2008 | Schwindt |
| 7,497,833 B2 | 3/2009 | Miller |
| 7,556,622 B2 | 7/2009 | Mark et al. |
| 8,172,771 B2 | 5/2012 | Miller et al. |
| 8,187,204 B2 | 5/2012 | Miller et al. |
| 8,202,229 B2 | 6/2012 | Miller et al. |
| 8,529,468 B2 * | 9/2013 | Hoffa et al. .................. 600/567 |
| 2001/0014785 A1 | 8/2001 | Sussman et al. |
| 2002/0045840 A1 | 4/2002 | Voegele et al. |
| 2002/0077565 A1 | 6/2002 | Burdorff et al. |
| 2002/0082519 A1 | 6/2002 | Miller et al. |
| 2002/0120212 A1 | 8/2002 | Ritchart et al. |
| 2002/0138047 A1 | 9/2002 | Lopez |
| 2002/0156365 A1 | 10/2002 | Tsekos |
| 2003/0018281 A1 | 1/2003 | Huitema |
| 2003/0073929 A1 | 4/2003 | Baltschun et al. |
| 2003/0087423 A1 | 5/2003 | Haywood et al. |
| 2004/0222137 A1 | 11/2004 | Hashimoto |
| 2004/0222145 A1 | 11/2004 | Onoue et al. |
| 2005/0049521 A1 | 3/2005 | Miller et al. |
| 2005/0085838 A1 | 4/2005 | Thompson et al. |
| 2005/0113715 A1 | 5/2005 | Schwindt et al. |
| 2006/0129062 A1 | 6/2006 | Nicoson et al. |
| 2006/0155210 A1 | 7/2006 | Beckman et al. |
| 2006/0260994 A1 | 11/2006 | Mark et al. |
| 2008/0045833 A1 | 2/2008 | Defreitas et al. |
| 2008/0221443 A1 | 9/2008 | Ritchie et al. |
| 2009/0087249 A1 | 4/2009 | Flagle et al. |
| 2009/0088663 A1 | 4/2009 | Miller et al. |
| 2009/0088664 A1 | 4/2009 | Miller et al. |
| 2009/0088666 A1 | 4/2009 | Miller et al. |
| 2009/0204020 A1 | 8/2009 | Miller et al. |
| 2011/0245715 A1 | 10/2011 | Quick et al. |
| 2013/0053726 A1 | 2/2013 | Miller et al. |

FOREIGN PATENT DOCUMENTS

| | | |
|---|---|---|
| EP | 1908391 | 4/2008 |
| WO | WO 0197702 | 12/2001 |
| WO | WO 2006/123312 | 11/2006 |

OTHER PUBLICATIONS

Notice of Non-Compliant Amendment for U.S. Appl. No. 10/958,026 dated Apr. 20, 2005 (2 pages).

Final Office Action for U.S. Appl. No. 10/958,026 dated Aug. 9, 2005 (6 pages).

Advisory Action dated Nov. 2, 2005 for U.S. Appl. No. 10/958,026 (3 pages).

Office Action dated Dec. 23, 2005 for U.S. Appl. No. 10/958,026 (8 pages).

Office Action dated Oct. 26, 2006 for U.S. Appl. No. 10/958,026 (7 pages).

Advisory Action dated Jan. 16, 2007 for U.S. Appl. No. 10/958,026 (3 pages).

Office Action dated Mar. 7, 2007 for U.S. Appl. No. 10/958,026 (10 pages).

Office Action dated Aug. 17, 2007 for U.S. Appl. No. 10/958,026 (8 pages).

Office Action dated Dec. 21, 2007 for U.S. Appl. No. 10/958,026 (9 pages).

Office Action dated Aug. 16, 2007 for U.S. Appl. No. 11/132,034 (21 pages).

Office Action dated Feb. 1, 2008 for U.S. Appl. No. 11/132,034 (17 pages).

Final Office Action dated Jul. 9, 2007 for U.S. Appl. No. 10/958,026 (17 pages).

* cited by examiner

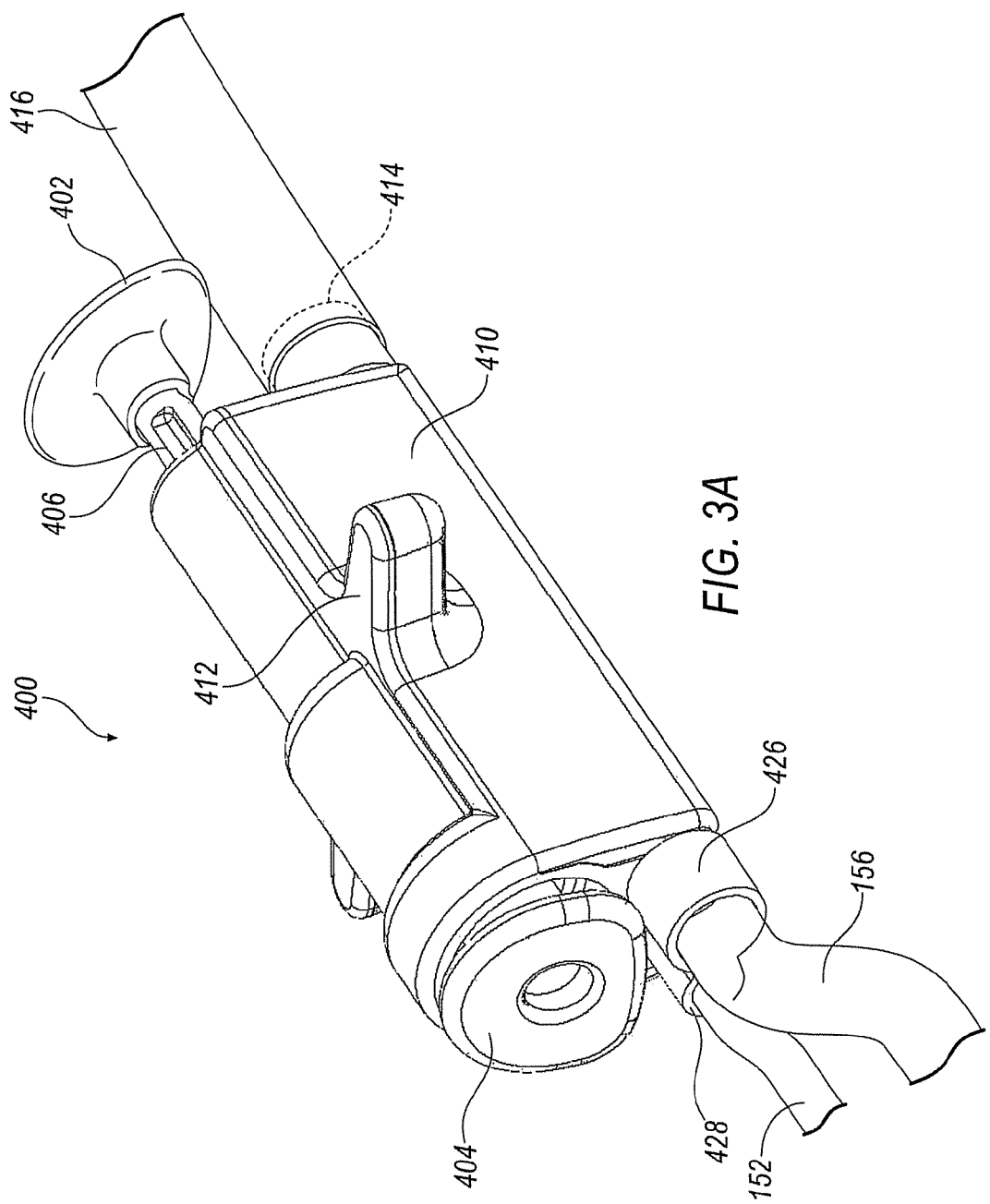

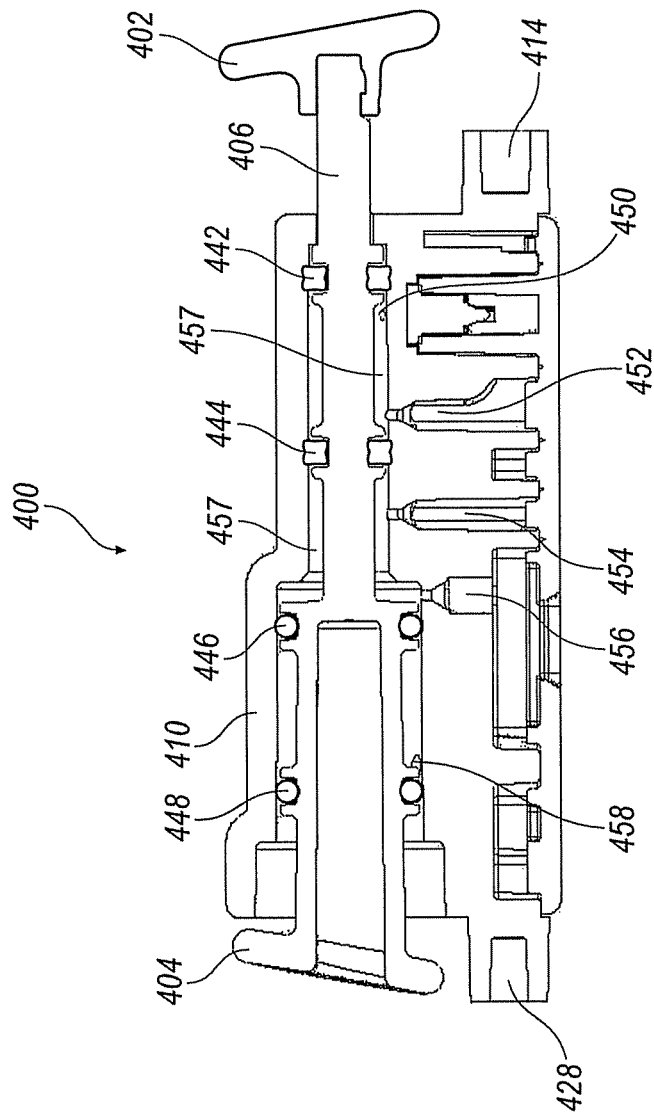

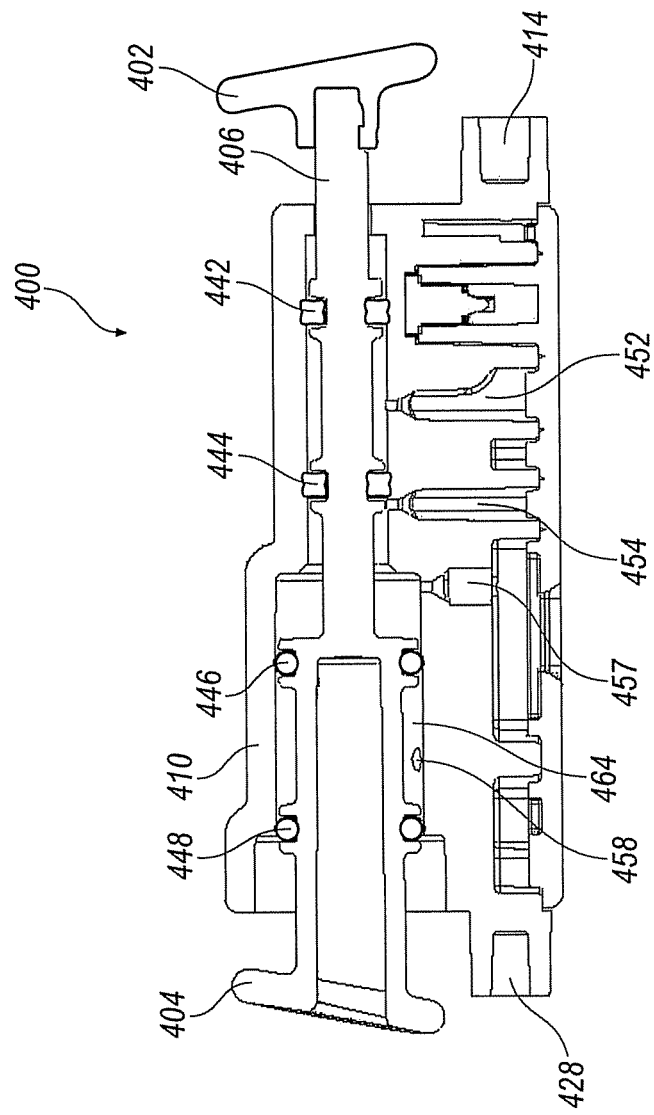

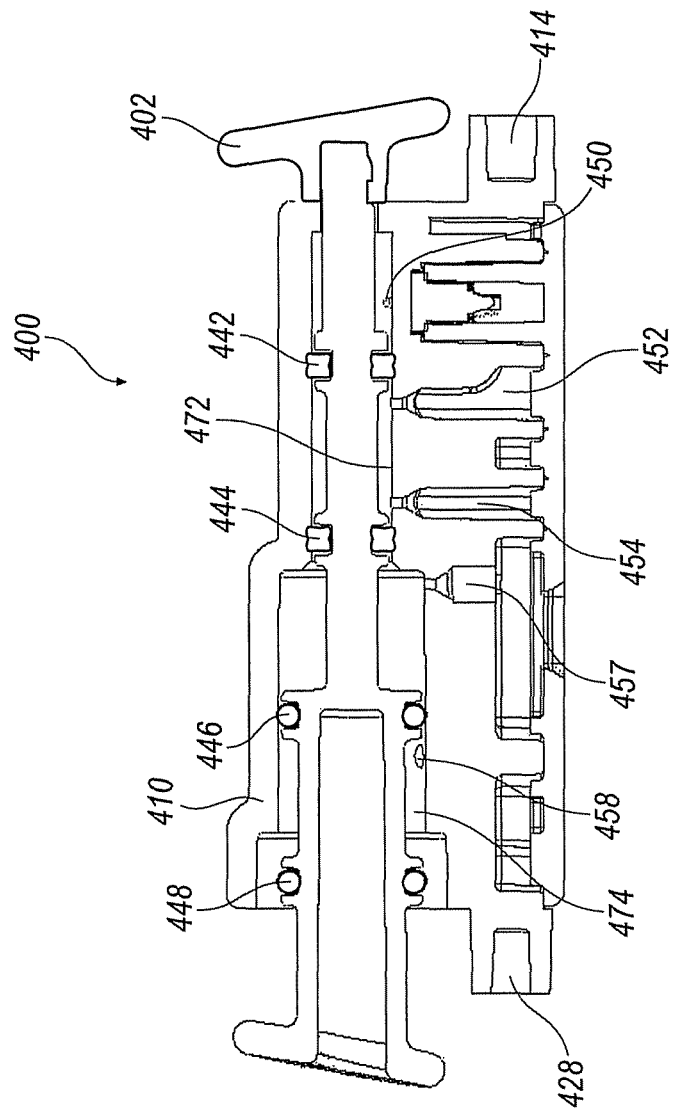

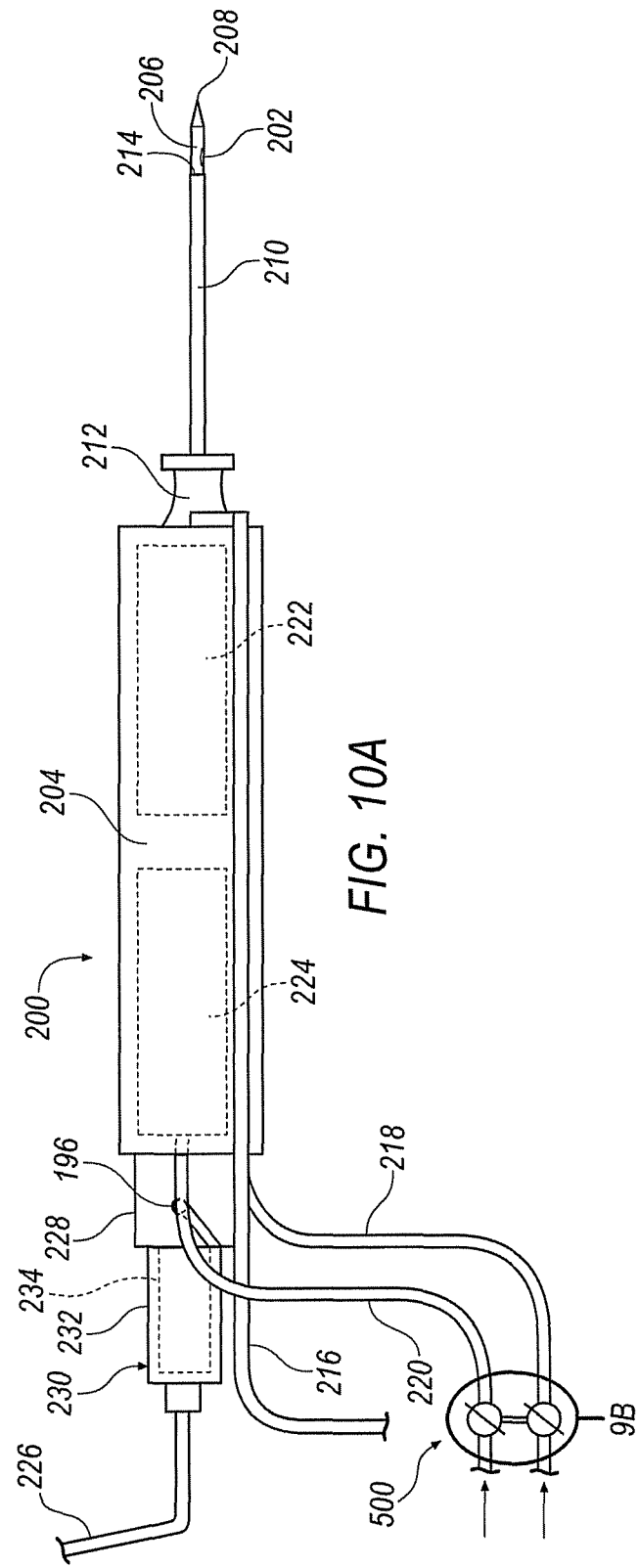

SURGICAL SYSTEM

RELATED APPLICATION DATA

The present application is a continuation of pending U.S. patent application Ser. No. 12/496,316, filed Jul. 1, 2009, the priority of which is claimed under 35 U.S.C. §120, and the contents of which is incorporated herein by reference in its entirety, as though set forth in full.

BACKGROUND

This disclosure relates to biopsy systems and methods for talking a biopsy. More specifically, this disclosure relates to biopsy systems for removing multiple tissue samples.

In the diagnosis and treatment of breast cancer, it is often necessary to remove multiple tissue samples from a suspicious mass. The suspicious mass is typically discovered during a preliminary examination involving visual examination, palpitation, X-ray, MRI, ultrasound imaging or other detection means. When this preliminary examination reveals a suspicious mass, the mass must be evaluated by taking a biopsy in order to determine whether the mass is malignant or benign. Early diagnosis of breast cancer, as well as other forms of cancer, can prevent the spread of cancerous cells to other parts of the body and ultimately prevent fatal results.

A biopsy of the breast, for example, can be performed by either an open procedure or a percutaneous method. The open surgical biopsy procedure first requires localization of the lesion by insertion of a wire loop, while using a visualization technique, such as X-ray or ultrasound. Next, the patient is taken to a surgical room where a large incision is made in the breast, and the tissue surrounding the wire loop is removed. This procedure causes significant trauma to the breast tissue, often leaving disfiguring results and requiring considerable recovery time for the patient. This is often a deterrent to patients receiving the medical care they require. The open technique, as compared to the percutaneous method, presents increased risk of infection and bleeding at the sample site. Due to these disadvantages, percutaneous methods are often preferred.

Percutaneous biopsies have been performed using either fine needle aspiration or core biopsy in conjunction with real-time visualization techniques, such as ultrasound, mammography (X-ray), MRI, PET, CT, terahertz technologies, etc. Fine needle aspiration involves the removal of a small number of cells using an aspiration needle. A smear of the cells is then analyzed using cytology techniques. Although fine needle aspiration is less intrusive than an open procedure, only a small amount of cells are available for analysis. In addition, this method does not provide for a pathological assessment of the tissue, which can provide a more complete assessment of the stage of the cancer, if found. In contrast, in core biopsy a larger fragment of tissue can be removed without destroying the structure of the tissue. Consequently, core biopsy samples can be analyzed using a more comprehensive histology technique, which indicates the stage of the cancer. In the case of small lesions, the entire mass may be removed using the core biopsy method. For these reasons core biopsy is preferred, and there has been a trend towards the core biopsy method, so that a more detailed picture can be constructed by pathology of the disease's progress and type.

The first core biopsy devices were of the spring advanced, "Tru-Cut" style consisting of a hollow tube with a sharpened edge that was inserted into the breast to obtain a plug of tissue. This device presented several disadvantages. First, the device would sometimes fail to remove a sample, therefore, requiring additional insertions. This was generally due to tissue failing to prolapse into the sampling notch. Secondly, the device had to be inserted and withdrawn to obtain each sample, therefore, requiring several insertions in order to acquire sufficient tissue for pathology.

Vacuum assisted core biopsy devices were subsequently developed that required only a single insertion into the biopsy site to remove multiple tissue samples. An example of a vacuum assisted core biopsy device incorporates a tube within a tube design that includes an outer piercing needle having a sharpened end for piecing the tissue. The outer tube has an opening for receiving tissue. An inner tube is slidingly disposed within the outer tube, and serves to cut tissue that has prolapsed into the opening in the outer cannula. A vacuum is used to draw the tissue into the opening in the outer cannula.

Vacuum assisted core biopsy devices are available in handheld (for use with ultrasound) and stereotactic (for use with X-ray) versions. Stereotactic devices are mounted to a stereotactic unit that locates the lesion and positions the needle for insertion. In preparation for a biopsy using a stereotactic device, the patient lies face down on a table and the breast protrudes from an opening in the table. The breast is then compressed and immobilized by two mammography plates. The mammography plates create images that are communicated in real-time to the stereotactic unit. The stereotactic unit then signals the biopsy device and positions the device for insertion into the lesion by the operator.

In contrast, when using the handheld model, the breast is not immobilized. Rather the patient lies on her back and the doctor uses an ultrasound device to locate the lesion. The doctor must then simultaneously operate the handheld biopsy device and the ultrasound device.

While the vacuum assisted core biopsy device presented an advancement in the field of biopsy devices, several disadvantages remain with some of the currently marketed devices. For example, existing biopsy devices include multiple tubes to properly operate the device. Because the tubes are attached to various components of the biopsy device, all of these tubes (including tubes that do not come into contact with bodily fluids) are disposed of at the conclusion of the procedure, leading to waste and increased expense.

Another issue with current biopsy devices is insuring proper placement of a filter in a tissue collection chamber. Known biopsy devices, such as that disclosed in commonly owned U.S. patent application Ser. No. 11/132,034, the contents of which are incorporated herein in its entirety, include a filter body that is positioned with a tissue collection chamber. Vacuum is drawn through tissue collection chamber such that resected tissue cores are directed into the filter and retained therein for later examination, while blood and other fluids are pulled through the filter to exit the collection chamber. Once a biopsy cycle is completed, the filter may be removed from the tissue collection chamber, and the tissue cores may be retrieved for examination.

Because the filter is a separate removable piece from the collection chamber, during assembly of the biopsy device it may be inadvertently omitted from the collection chamber. Alternatively, the filter may be taken out of the collection chamber prior to use, but not replaced. However, if the filter is not properly placed within the tissue collection chamber, the resected tissue is not properly retained within the filter. Instead, resected tissue cores may pass through the tissue collection chamber and become lodged in the vacuum line, disabling the biopsy device and prohibiting examination of the cores. In some instances, the cores may also be flushed to a separate vacuum canister, along with other waste, in which case the physician may be able to recover the cores.

Another issue with prior art devices relates to different modes of operation of the device. For example, as described in commonly owned U.S. patent application Ser. No. 11/132,034, the contents of which are incorporated herein in its entirety, the biopsy device is operable in several different modes, including a "biopsy mode" and a "lavage mode." In the biopsy mode, the device is taking tissue cores and delivering the cores to the tissue filter via the vacuum line. In the lavage mode, the biopsy device cylinder is vented, and then a saline flush is introduced to clear out biopsy cavity, as well as clearing out bodily fluids from the biopsy device. A console provides actuation mechanisms to switch between various modes. And if a physician attempts to tale tissue cores while the device is set in the lavage mode, the device will not operate, triggering malfunction alarms.

Further, for those biopsy devices that are used with Magnetic Resonance Imaging (MRI), the console must be placed outside of MRI suite where the device is being used. Thus, to switch between the modes, the physician is required to walk out of the suite thereby, leaving the patient's side, each time it is desired to switch between modes.

Another issue that may be experienced by users of the biopsy devices is not being able to cock the biopsy device (i.e., preparing the device for firing by retracting the outer cannula) for taking biopsy cores while the device is in the lavage mode. To prepare the device for taking tissue cores, the device requires pressure from the console to cock the device. The pressure is only available while in the biopsy mode. And if the device is cocked and fired in the lavage mode, the tissue aperture will be open, causing additional trauma to the patient.

Even if the biopsy device is in the cocked position, there still may be an issue with acquiring tissue. For example, if the device is in the cocked position, but the aperture is closed (the inner cutting cannula advanced forward), the aperture will not open during the biopsy cycle, and therefore tissue cores will not be acquired.

If the remote firing valve is not placed in the correct position, such as placing the remote valve between the cocked the fired positions so as only to partially cock the device, the device will not fully fire during the procedure and tissue may not be fully cut during the biopsy cycles.

BRIEF SUMMARY

A surgical device is disclosed that comprises a cutting element, a biopsy line, a motor line, and a vacuum line. The cutting element includes an outer cannula and an inner cannula. The biopsy line is operatively connected to a control console for moving the inner cannula within the outer cannula to cut tissue cores. The motor line is operatively connected to the control console for operating the surgical device. The vacuum line is operatively connected to the inner cannula. A selectively openable tissue filter is operatively connected to the inner cannula, and is also connected to the vacuum line.

BRIEF DESCRIPTION OF THE DRAWINGS

FIG. 3A is a perspective view of a remote valve for use with the surgical device of FIG. 1A.

FIGS. 3B-3D are cross-sectional views of the remote valve of FIG. 3A, in various operational positions.

FIG. 10A is a side view of a surgical device with a remote mode toggle system.

DETAILED DESCRIPTION

Figure 1A:
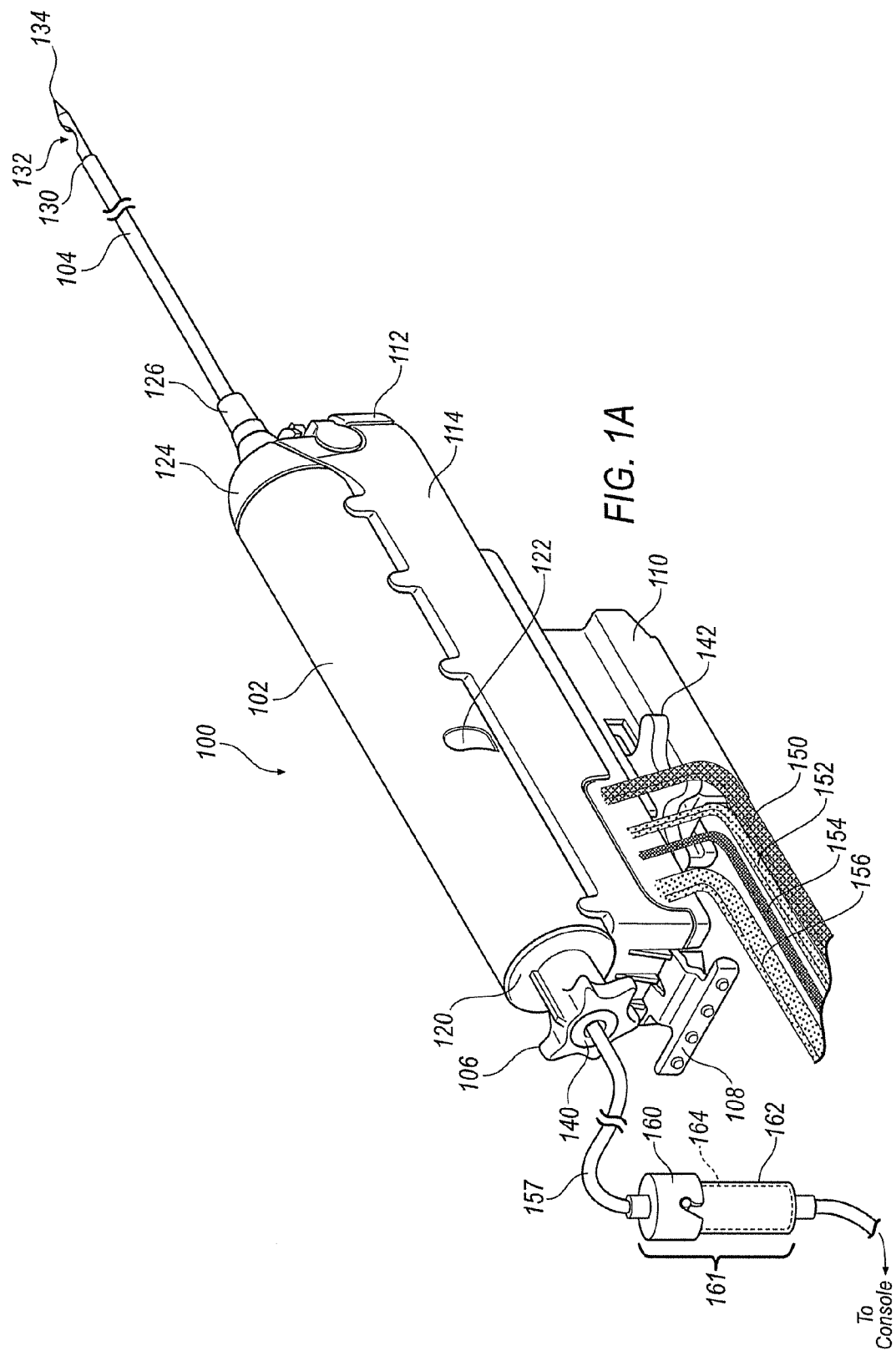
FIG. 1A is a perspective view of a stereotactic surgical device.

Referring now to the drawings, the preferred illustrative embodiments of the present disclosure are shown in detail. Although the drawings represent some embodiments of the present disclosure, the drawings are not necessarily to scale and certain characteristics may be exaggerated to better illustrate and explain the present disclosure. Further, the embodiments set forth herein are not intended to be exhaustive or otherwise limit or restrict the disclosure to the precise forms and configurations disclosed in the following detailed description.

Figure 1B:
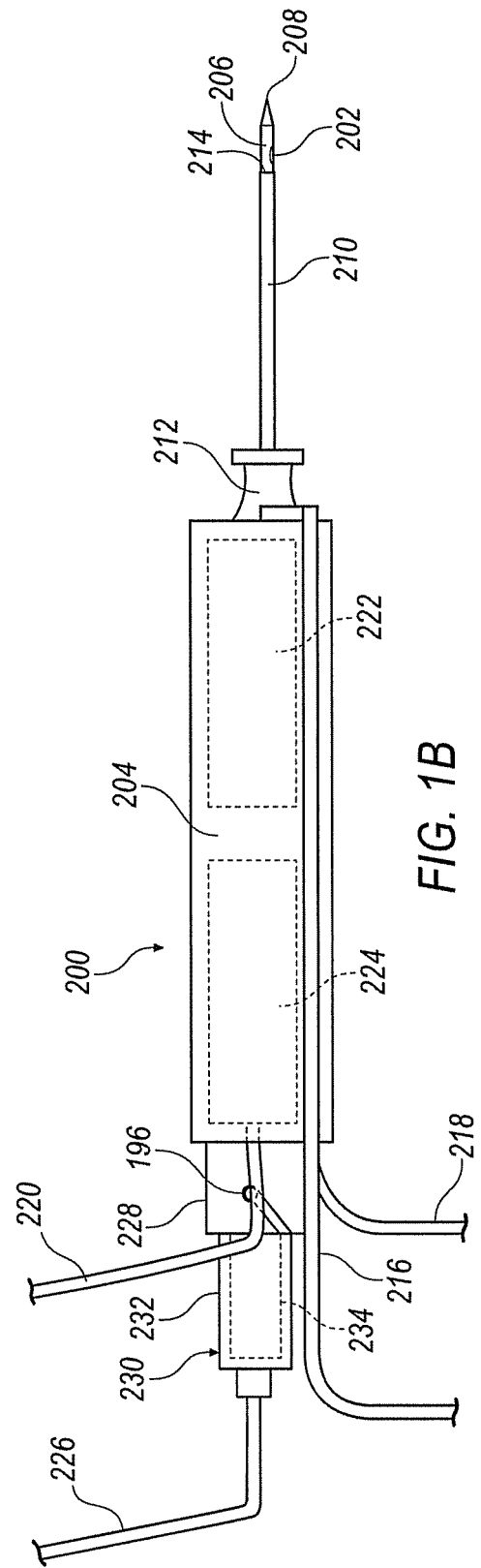
FIG. 1B is an elevational view of a handheld surgical device.

Referring now to the drawings, FIG. 1A illustrates a surgical device 100. Surgical device 100 is configured as a stereotactic type surgical device such as shown in commonly owned U.S. patent application Ser. No. 11/132,034. A handheld surgical device 200, such as shown in commonly owned U.S. patent application Ser. No. 10/970,269, the contents of which are incorporated herein by reference in its entirety, is shown in FIG. 1B and will be explained below in further detail.

Surgical device 100 includes an outer housing 102, an introducer cannula 104, and a rotator 106. Surgical device 100 is positioned on a cradle top 114. An adapter 112 connects cradle top 114 to a bracket 110. In an embodiment, surgical device 100 including outer housing 102, introducer cannula 104, rotator 106, and cradle top 114 are disposable. Adapter 112 is positioned underneath surgical device 100 and is typically left attached to a positioning table for reuse with another surgical device 100. A latch lever 108 is operable to release cradle top 114 from adapter 112. Outer housing 102 is provided to hold moving components and seals internal to surgical device 100 between a proximal cap 120 and a front cap 124. Introducer cannula 104 is fixed to an introducer hub 126 that removably attaches to a cutting element 132 and adapter 112. During a procedure, introducer cannula 104 is positioned to allow for the insertion of surgical device 100 near the target site. When surgical device is positioned, a cutting element 132 protrudes (shown here in a fired position) at a distal end 130 of introducer cannula 104. In one embodiment, cutting element 132 also includes a trocar tip 134 that is designed to easily penetrate tissue with minimal damage. Alternatively, in one embodiment, cutting element 132 may include a blunt tip end that is not sharp. The blunt tip embodiment, which may include a generally hemispherical shape, is useful where the site of interest is close to the back plate of the compression device as the trocar tip may extend too far and exit the opposite side of the breast from the insertion point.

Figure 2A:
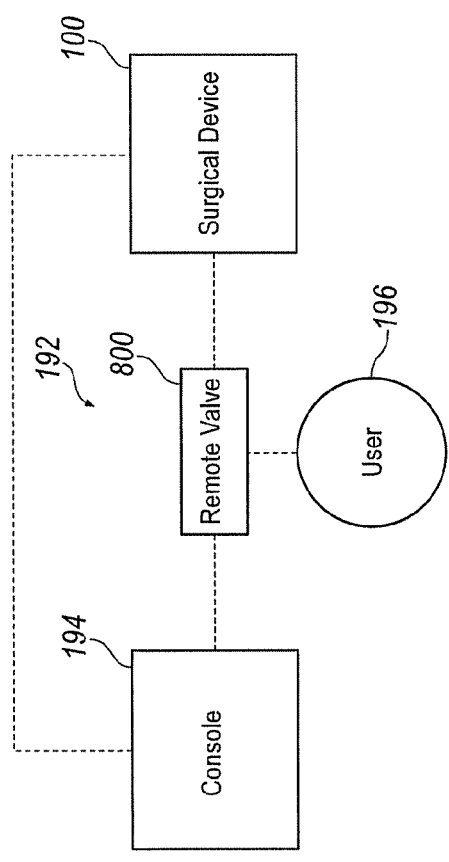
FIG. 2A is a schematic view of a surgical system that incorporates a surgical device of FIG. 1A.

Referring now to FIG. 2A, a schematic of a surgical system 192 for use with surgical device 100 is shown. Surgical system 192 includes a control console 194, a remote valve 400, a user 196, and surgical device 100. Surgical device 100 is operatively connected to console 194 and a remote valve 400. User 196 is typically a surgeon and is able to control each of console 194, remote valve 400, and surgical device 100. Console 194 provides both air pressure and vacuum, as well as control logic, to surgical device 100. In one exemplary embodiment, surgical device 100 is primarily controlled by user 196 at remote valve 400 during the high patient stress time of firing an outer cannula 131 (for those embodiments with a trocar tip distal end), which is conveniently located between surgical device 100 and console 194. Remote valve 400 is shown in FIG. 3 and will be explained below in further detail.

Referring back to FIG. 1A, a saline line 154, a firing line 152, a motor line 150, and a biopsy line 156 are attached to the surgical device 100. Lines 150-156 are also operatively attached to control console 194 for controlling surgical device 100. In one embodiment, cradle top 114 is a housing that receives, secures, and covers the internal attachment of a distal end of saline line 154, firing line 152, motor line 150, and biopsy line 156. Cradle top 114 may be constructed of plastic or other suitable materials. In the embodiment shown, bracket 110 attaches to adapter 112 by a screw. The shown bracket 110 is engaged or disengaged from a stereotactic table by rotating attachment wheel 142. It is appreciated, however, that the bracket 110 may be of other suitable configurations to permit use of the surgical device with other surgical tables.

Rotator 106 includes a fitting 140 where a vacuum line 157 attaches to provide vacuum to cutting element 132. A rotation indicator 122 may be provided that describes the rotary position of cutting element 132. Rotation indicator 122 is a window that is cut through outer sleeve 102 so as to expose an inner portion having indicia that rotates along with rotator 106. In general, when rotator 106 is turned by a user, the rotary position of cutting element 132 is shown by rotation indicator 122. Typically, a numeral is shown at rotation indicator 122 describing the position of cutting element 132 in a manner similar to a clock face. For example, the indicia of rotation indicator 122 may include numerals such as one (1) through twelve (12) o'clock. In this way, a surgeon can immediately and intuitively determine the rotary position of cutting element 132 by viewing rotation indicator 122. Moreover, rotation indicator 122 is highly visible and does not require special training to determine the angular position of cutting element 132. Alternatively, any indicia may be used for rotation indicator 122 to indicate the position of cutting element 132.

The components of surgical device 100 are configured such that the turning of rotator 106 is not overly burdensome on the operator (e.g., a surgeon). Thus, the torque required to turn rotator 106, and necessarily cutting element 132 including a sampling aperture, is low. Thus, low grip strength and low torque is required to turn rotator 106 and cutting element 132.

In one embodiment, the vacuum line 157 is attached to a cap member 160 that removably connects to a tissue collection assembly. The tissue collection assembly includes a can member 162 and a selectively removable filter member 164. The selectively removable filter member 164 (shown in phantom in FIG. 1A) is positioned within the cap member 160. When the tissue collection assembly is removably secured to the cap member 160, the filter member 164 is positively retained within the can member 162. The tissue collection assembly will be further described below in connection with FIGS. 6-8.

FIG. 3A is a perspective view of the remote valve 400. Remote valve 400 includes a firing button 402, a cocking button 404, an actuator rod 406, a remote valve body 410, and finger bars 412. Air pressure from control console 194 enters remote valve 400 at a console inlet 414. The console inlet 414 is attached to console 194 via pressure line 416. Firing line 152 (see FIG. 1) is sealingly engaged to a firing port 428. Biopsy line 156 (see FIG. 1) is sealingly engaged to a biopsy port 426. When firing button 402 is pressed toward remote valve body 410, pressure is vented from firing port 428 and firing line 152 and outer cannula 131 (shown in FIG. 1A) is rapidly extended distally (described in detail in U.S. patent application Ser. No. 11/132,034). Pressure is then applied to biopsy port 426 and biopsy line 156. When cocking button 404 is pressed towards remote valve body 410, pressure is vented from biopsy port 426 and biopsy line 156 and pressure is then applied to firing port 428 and firing line 152.

Vacuum line 157 is connected to fitting 140, which is in communication with an inner cannula (not shown). The inner cannula (described in detail in U.S. patent application Ser. No. 11/132,034) is disposed with outer cannula 131 and reciprocates across a tissue opening formed in cutting element 132 to cut tissue cores. Vacuum line 157 provides vacuum from console 194 and is used to pull fluids, tissue, and/or generally remove irrigation from the target site. As described above, selectively removable tissue collection assembly 161 is connected in-line with vacuum line 157 where harvested tissue may be collected for analysis. Console inlet 414 is connected to a pressure line 416 which is controlled by console 194.

Saline line 154 is connected to surgical device 100 (see FIG. 1) and may also be connected to a selectively closable valve that includes a stopcock or a fitting (i.e., a luer lock) that may be selectively opened and closed, as shown in U.S. patent application Ser. No. 11/132,034. Saline port 154 connects to a saline source (e.g., a saline bag) but may also be connected to other types of liquid sources such as bag containing a treatment fluid. Saline line 154 may also include an injection port that allows a user to inject substances to be transported to the target site. The stopcock or fitting may also be selectively activated close-off the saline source from saline line 154 allowing saline line 154 to be vented to the atmosphere. This allows the user to selectively aspirate the target site, vacuum line 157, and a collection canister, for example, after tissue is resected to remove fluids from the system.

FIG. 3B is a cross-sectional view of remote valve 400 in a cocked position. Remove valve 400 includes a first port 450, a second port 452, a third port 454, a fourth port 456, and a fifth port 458. First port 450 and fifth port 458 are connected to firing port 428 and firing line 152. First port 450 also includes a one-way check valve that does not allow pressure from firing line 152 to flow into remote valve 400. For example, if the console is turned off or inlet air to remote valve 400 is removed, then the check valve will keep the device in the cocked position. Second port 452 is connected to console inlet 414 and a pressure source. Third port 454 is connected to biopsy port 426 and biopsy line 156. Fourth port 456 is open to the atmosphere and serves as a vent.

Actuator rod 406 extends through remote valve 400 and includes a first seal 448, a second seal 446, a third seal 444, and a fourth seal 442. Seals 446 and 448 may be configured as o-rings. Seals 442 and 444 may be configured as quad-rings to prevent pressurized air from first port 450, and third port 454 from venting as seals 442, 444 pass over them. As actuator rod 406 is traversed through remote valve body 410, seals 442, 444, 446, 448 create air flow regions for ports 458, 456, 454, 452, 450 to selectively connect to each other or vent to the atmosphere to control operation of surgical device 100. As shown in FIG. 3B, remote valve 400 is in a cocked position where second port 452 is connected to first port 450 by way of seals 442 and 444 that and a cavity 457 between actuator rod 406 and remote valve body 410. The cocked position provides that an air motor and a spool are in their proximal most positions within surgical device 100. If the console were turned off while surgical device 100 was in the cocked position, air would remain in an exhaust chamber within the device and surgical device 100 would remain in the cocked position until remote valve 400 was further manipulated due to the check valve.

FIG. 3C is a cross-sectional view of remote valve 400 in an intermediate position between a cocked position (see FIG. 3B) and a fired position (see FIG. 3D). Seal 442 is positioned over first port 450. Second port 452 is effectively isolated by first seal 442 and second seal 444. Moreover, first seal 448 is prepared to disengage from the inner periphery of remote valve body 410 and become free to the surrounding atmosphere (see FIG. 3D below).

FIG. 3D is a cross-sectional view of remote valve 400 in a fired position. First seal 448 is open to the atmosphere resulting in fifth port 458, firing port 428, and firing line 152 being exhausted. For example, port 458 is open to the atmosphere via passage 474 as first seal 448 is no longer contacting remote valve body 410. The fired position of FIG. 3D contrasts with the embodiment of FIG. 3B where first seal 448 is in sealing contact with remote valve body 410 and second seal 446 and first seal 448 sealing port 458 therebetween.

Because first seal 448 is an o-ring and is exhausted directly to the atmosphere across the entire circumference of the o-ring, rather than through a port (see FIGS. 3B and 3C), a larger volume of air may be exhausted. Such a rapid exhaust assists in the rapid deployment, or firing, of the outer cannula 131.

Third port 454 is then connected to second port 452, console inlet 414, and a pressure source from a console (not shown). When third port 454 and second port 452 are connected by virtue of first seal 442, second seal 444 and cavity 472, pressure is applied to biopsy cavity 408 and the air motor within surgical device 100 is moved forward in biopsy mode slightly after a spool is fired forward.

Referring now to FIG. 1B, a handheld surgical device 200 is shown. Surgical device 200 includes a cutting element 202 mounted to an outer housing 204. The cutting element 202 includes an outer cannula 206 terminating in a cutting tip 208. An introducer cannula 210 may be fixed to an introducer hub 212 that removably attaches to cutting element 202 and housing 204. During a procedure, introducer cannula 210 is positioned to allow for the insertion of surgical device 200 near the target site. When the surgical device 200 is positioned, the cutting element 202 protrudes at a distal end 214 of introducer cannula 210.

Figure 2B:
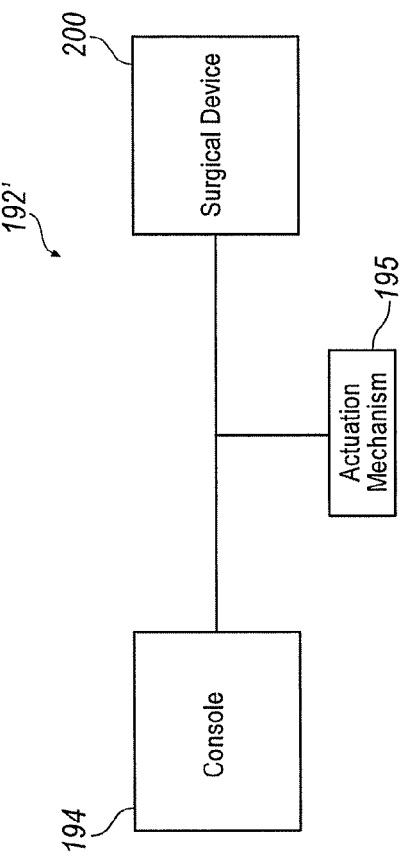
FIG. 2B is a schematic view of a surgical system that incorporates a surgical device of FIG. 1B.

Like surgical device 100, surgical device 200 includes a saline line 216, a motor line 218, and a biopsy line 220. One end of saline line 216 is operatively connected to outer cannula 206 to selectively deliver saline to cutting element 202. One end of motor line 218 is connected to a motor 222 (shown in phantom). And one end of biopsy line 220 is operatively connected to a pneumatic cylinder 224 (also shown in phantom). The opposite ends of the saline, motor, and biopsy lines are operatively connected a control console 194, as shown in FIG. 2B. An actuation mechanism 195, such as a foot pedal is connected to control console 194 and serves to selectively power biopsy device 200 on and off while the control console 194 is placed in various operational modes. For example, when control console 194 is placed in the biopsy mode, actuation device 195 is depressed, thereby powering motor line 218 and biopsy line 220 to take tissue cores. When actuation device 195 is not depressed while the control console 194 is in the biopsy mode, no tissue cores are being taken.

In one embodiment, a cap member 228 is secured to a proximal end of the outer housing 204. In another embodiment (not shown), cap member 228 is positioned remotely from outer housing 204 by a length of tubing, similar to the configuration of FIG. 1A. A tissue collection assembly 230 removably connects to cap member 228 in a similar manner as shown in FIG. 1A. More specifically, the tissue collection assembly includes a can member 232 and a filter member 234. The selectively removable filter member 234 (shown in phantom in FIG. 1B) is positioned within the cap member 232. When the tissue collection assembly is removably secured to the cap member 232, the filter member 234 is positively retained within the can member 232. A proximal end of the can member 232 is connected to a vacuum line 226. One end of vacuum line 226 is operatively connected to the control console. The tissue collection assembly is also connected to an inner cutting cannula that is slidingly engaged with outer cannula 206. The tissue collection assembly will be further described below in connection with FIGS. 6-8.

Figure 4:
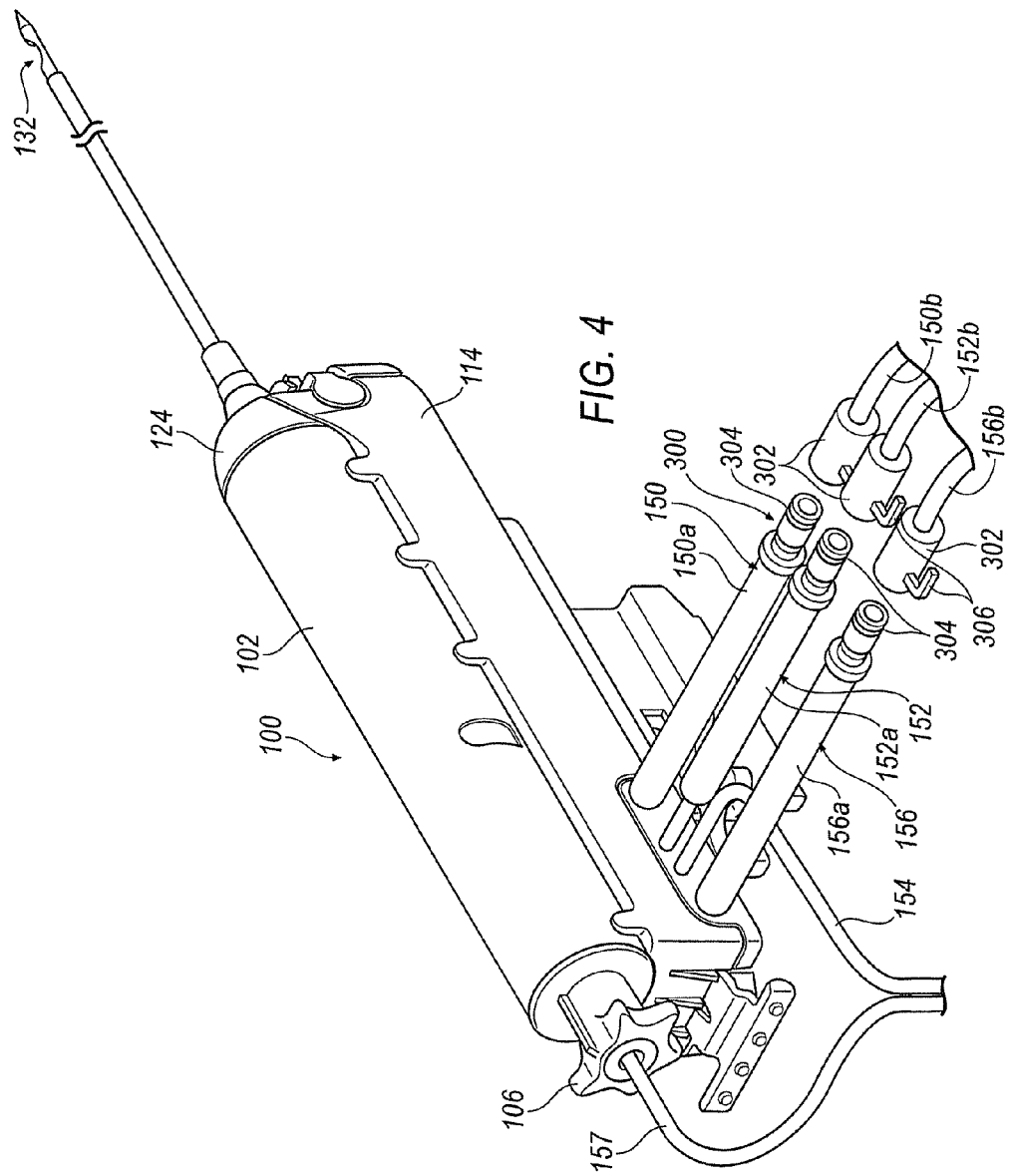
FIG. 4 is a perspective view of a surgical device with selectively removable tubing.

Referring now to FIG. 4, one feature of the disclosure will now be described. As discussed above, the surgical devices 100 and 200 include a number of tube or lines that assist in operation of the respective devices. Using the stereotactic embodiment as an example, there are several lines that come in contact with bodily fluids during operation of biopsy device 100, and as such, must be disposed of after the conclusion of the procedure. For example, the saline line 154 and the vacuum line 157 both come into contact with bodily fluids. The remainder of the lines, the firing, motor and biopsy lines 152, 150 and 156 do not come into contact with bodily fluids. As such, having these lines completely disposable generates unnecessary waste and increased expense.

To address this concern, in the arrangement shown in FIG. 4, the firing, motor and biopsy lines 152, 150 and 156 are each formed as having first and second sections. The first section has a relatively short length of tubing 154a, 150a, and 156a, each having one end extending into the cradle 114 and distal ends of each of the first sections (154a, 150a, 156a) are fixedly attached to the internal components of the biopsy device 100. Fixedly attached to proximal ends of the tubing 154a, 150a, and 156a are connector members 300. Separate, non-disposable second sections of firing, motor and biopsy lines 154b, 150b, and 156c have each have mating connector members 302 attached to a distal end thereof. In one exemplary embodiment, the connector members 300 are configured as male members, while the connector members 302 are configured as female members that include a passageway that selectively receives the male connector members 300. The male members 300 may further include sealing rings 304 to maintain a fluid-tight connection. The female members 302 further include latch members 306 to selectively secure the tubing 154a, 150a, and 156a to firing, motor and biopsy lines 154b, 150b, and 156b. It is understood that tubing 154a, 150a, and 156a may be provided with female connectors 302 and firing, motor and biopsy lines 154b, 150b, and 156b may be provided with male connectors 300 without departing from the disclosure. It is also understood that other types of mating connector members may be employed.

In operation, once a biopsy procedure is complete, saline line 154 and vacuum line 157 are disconnected from the console 194. Tubing sections 154a, 150a and 156a are also each disconnected from second sections firing, motor and biopsy lines 154b, 150b, and 156b by actuating the latches 306 or other suitable release mechanisms on each. Once disconnected, biopsy device 100, saline and vacuum lines 154 and 157, and tubing 154a, 150a, and 156a are disposed of. However, firing, motor and biopsy lines 154b, 150b, and 156b, which are all connected to remote valve 400 and console 194, may be retained for future use.

Figure 5:
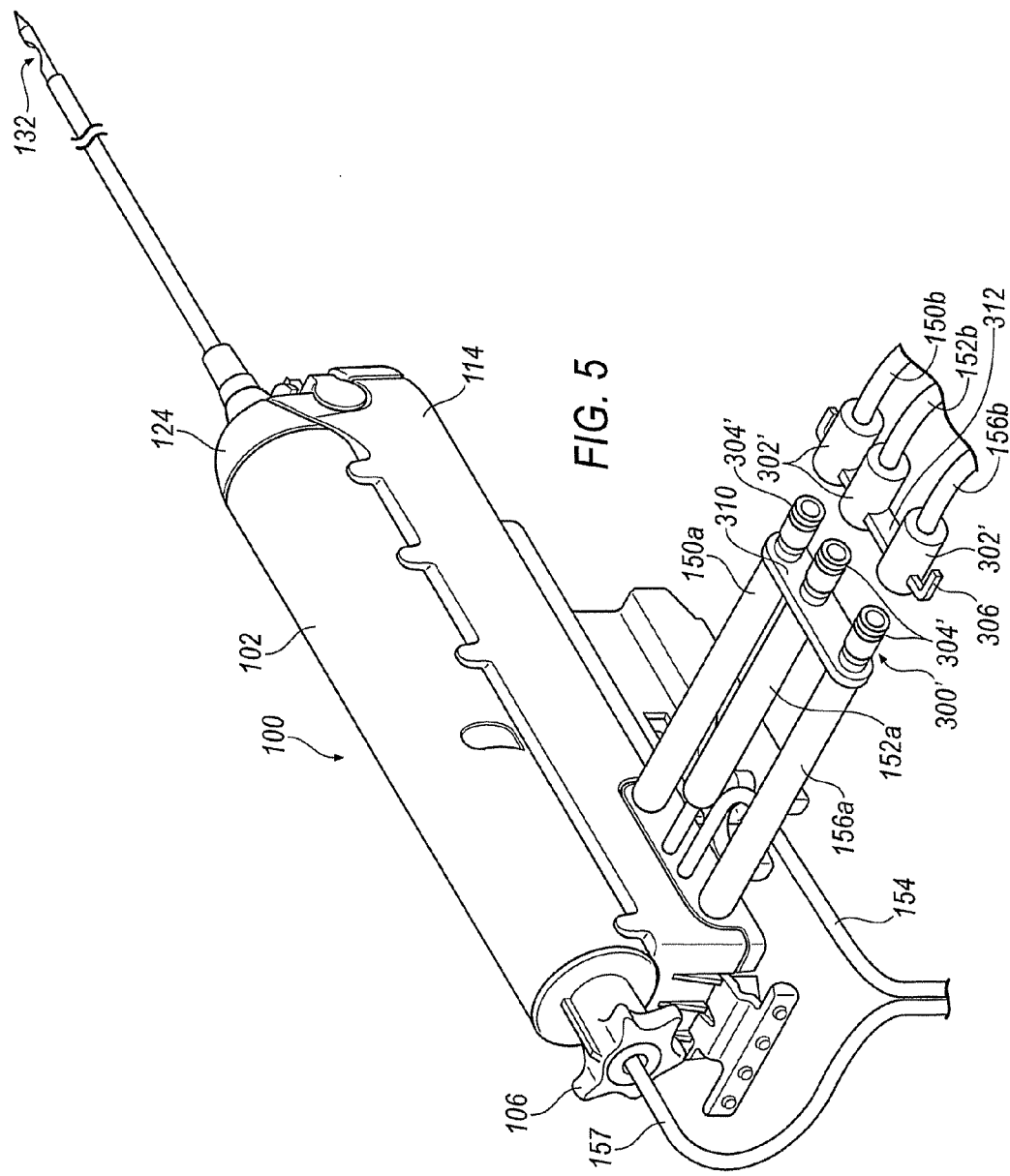
FIG. 5 is a perspective view of a surgical device with an alternative arrangement of selectively removable tubing.

While FIG. 4 illustrates that firing, motor and biopsy lines 154b, 150b, and 156b must be individually connected and latched to corresponding tubing 154a, 150a, and 156a, FIG. 5 illustrates an alternative arrangement. In the arrangement of FIG. 5, tubing 154a, 150a, and 156a are connected together with a manifold 310. Male connectors 300' for each of tubing 154a, 150a, and 156a extend outwardly from manifold 310.

Similarly, firing, motor and biopsy lines 154b, 150b, and 156b are connected together by a mating manifold 312. Female connectors 302' are integrally connected with manifold 312 with a distal end extending outwardly from a mating face of manifold 312. Latch members 306 are positioned on either side of manifold 312. The male connectors 300' are received within female connectors 302' with manifolds 310 and 312 coming together. Latch members 306 are then actuated to positively secure the manifolds 310 and 312, and hence the firing, motor, and biopsy lines 154b, 150b, and 156b to tubing 154a, 150a, and 156a.

Once a biopsy procedure is complete, saline line 154 and vacuum line 157 are disconnected from the console 194. Tubing 154a, 150a and 156a are also each disconnected from firing, motor and biopsy lines 154b, 150b, and 156b by actuating the latches 306 on manifold 312. Once the latches are actuated, manifold 312 is separated from manifold 310, thereby disconnecting tubing 154a, 150a, and 156a from firing, motor and biopsy lines 154b, 150b, and 156b. Once disconnected, biopsy device 100, saline and vacuum lines 154 and 157, and tubing 154a, 150a, and 156a (along with manifold 310) are disposed of. However, firing, motor and biopsy lines 154b, 150b, and 156b, which are all connected to remote valve 400 and console 194, may be retained for future use.

While the arrangements for reusable firing, motor and biopsy lines 154b, 150b and 156b shown in FIGS. 4 and 5 have been described in the context of biopsy device 100, it is also understood that these arrangement may also be used in connection with biopsy device 200. For example, biopsy device 200 includes two lines that are come into contact with bodily fluids, saline line 216 and vacuum line 226. However motor line 218 and a biopsy line 220 do not come into contact with bodily fluids and thus may be reused after complete of a biopsy procedure. Therefore, motor line 218 and biopsy line 220 may be provided with connectors 300, 302 (not shown) and/or manifolds 310 and 312 to provide for reusability of the motor and biopsy lines 218 and 220.

Figure 6:
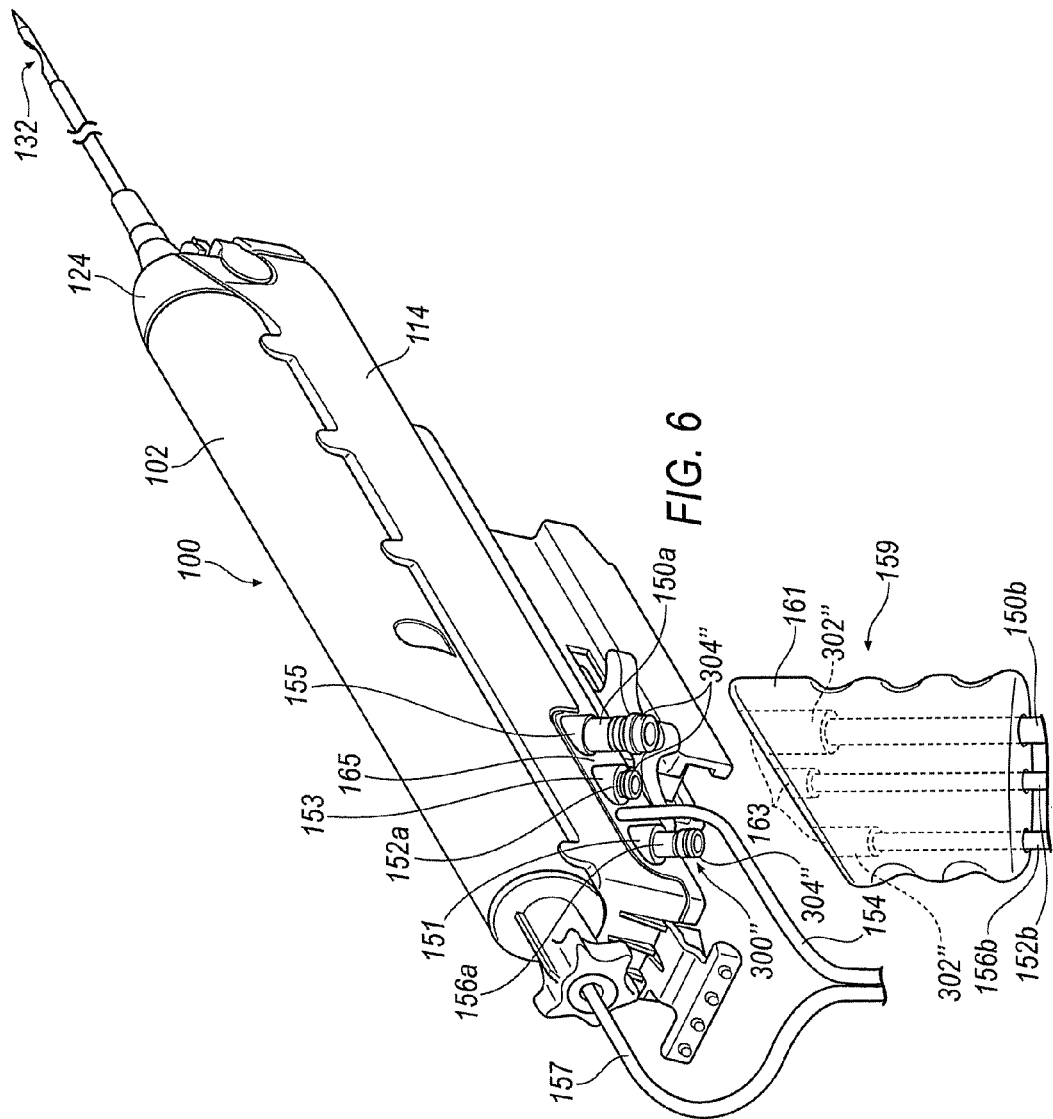
FIG. 6 is a perspective view of a surgical device with another alternative arrangement of selectively removable tubing.

FIG. 6 illustrates another alternative arrangement for quick connect/disconnect of firing, motor biopsy lines 156b, 152b, and 150b. In the arrangement of FIG. 6, tubing 156a, 152a, and 150a protrudes slightly from corresponding sleeves 151, 153, and 155 that are integrally molded to the cradle 114. Connectors 300" for each of tubing 156a, 152a, and 150a are secured on proximal ends of each tubing section. In one exemplary embodiment, connectors 300" are configured as male connectors 304".

A gripping block 159 is also provided. Gripping block 159 includes a housing 159 that into which distal ends of firing, motor, and biopsy lines 156b, 152b, and 150b are housed. Attached to distal ends of firing, motor, and biopsy lines 156b, 152b, and 150b are connectors that engage with connectors 300". The connectors attached to firing, motor, and biopsy lines 156b, 152b, and 150b are integrally seated within gripping block 159 such that a mating end 163 is positioned along a top surface of gripping block 159. In one exemplary embodiment, the connectors formed in gripping block 159 are female connectors 302".

In one embodiment, the top surface of gripping block 159 is configured to be received within a small recess 165 formed on cradle 114 in a selectively removable arrangement such that gripping block 159 attaches to cradle 114. In such an arrangement, male connectors 300" are received within female connectors 302" and hence the firing, motor, and biopsy lines 154b, 150b, and 156b to tubing 154a, 150a, and 156a. A latch member (not shown) may be employed to positively secure gripping block 159 to cradle 114. Alternative snap-fit arrangements may also be employed.

Once a biopsy procedure is complete, saline line 154 and vacuum line 157 are disconnected from the console 194. Tubing 154a, 150a and 156a are also each disconnected from firing, motor and biopsy lines 154b, 150b, and 156b by detaching gripping block 159 from cradle 114. Once disconnected, biopsy device 100, saline and vacuum lines 154 and 157, and tubing 152a, 150a, and 156a are disposed of. However, firing, motor and biopsy lines 152b, 150b, and 156b, which are all connected to remote valve 400 and console 194, may be retained for future use.

Figure 7:
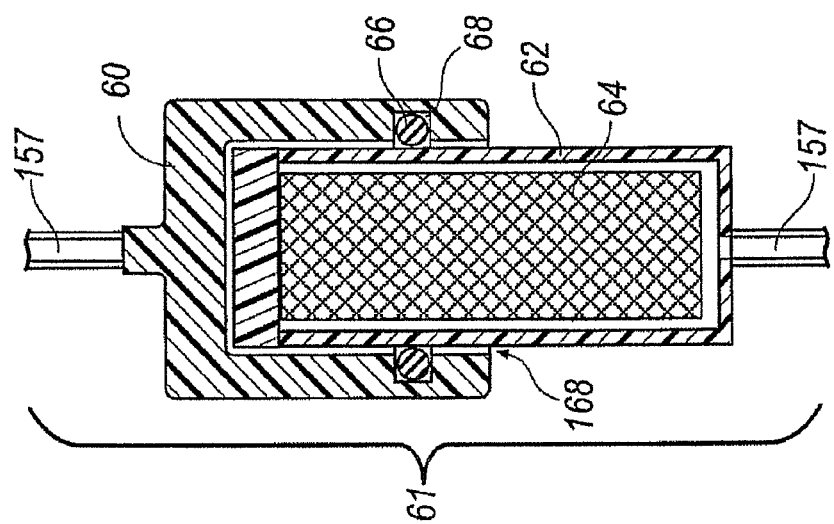
FIG. 7 is a cross-sectional view of a prior art tissue collection assembly.

Referring now to FIG. 7, a prior art tissue collection assembly 61 will now be described. As discussed above, tissue collection assemblies are used to collect the tissue cores obtained by biopsy devices 100, 200. Prior art tissue collection assemblies 61 comprise a cap member 60 that is attached to vacuum line 157, a generally hollow filter can 62 a filter member 64, and a seal member 66. In the embodiment shown in FIG. 1A, the vacuum line 157 is positioned on both ends of the tissue collection assembly 61. In other embodiments, the cap member 60 is connected directly to a proximal end of the biopsy device 200.

In the prior art assembly, filter member 64 is configured with a generally porous material so that fluids may pass through, while tissue cores are retained therein. Filter member 64 is removably positioned within filter can 62. Filter can 62, is received within an open end 168 of cap member 60 and secured to cap member 60 so as to selectively lock filter can 62 to cap member 60. In one particular arrangement, filter can 62 is configured with bayonet mounts (not seen in FIG. 6) that engage a mounting channel formed in cap member 60 (see FIG. 1A, for example). Seal member 66 is disposed around the exterior of filter can 62 and is received within mounting grooves 68 formed in an interior surface of cap member 60. Seal member 66 serves to maintain vacuum through in the biopsy device 100, 200 so as to continuously draw tissue cores into the tissue collection assembly 61.

During operation of biopsy devices 100, 200, vacuum is drawn through tissue collection assembly 61 such that resected tissue cores are directed into filter member 64 and retained therein for later examination. Blood and other fluids (such as saline) are pulled through filter member 64 to exit the filter can 62 and directed to a waste collection chamber (not shown). Once a biopsy cycle is completed, filter can 62 may be disengaged from cap member 60 and filter member 64 may be removed from filter can 62 so as to permit access to the tissue cores contained within the filter member 64. The tissue cores may then be retrieved from the filter member 64 for examination.

However, because filter member 64 is a separate removable piece from the filter can 62, during assembly of biopsy devices 100, 200, filter member 64 may be inadvertently omitted from filter can 62. Alternatively, filter member 64 may be taken out of filter can 62 prior to use, but not replaced. However, if filter member 64 is not properly placed within filter can 62, the resected tissue cores will not be properly retained within filter member 64. Instead, resected tissue cores may pass through the filter can 62 and become lodged in vacuum line 157, disabling biopsy devices 100, 200 and prohibiting examination of the cores. In some instances, the cores may also be flushed to the separate waste collection canister, along with other waste, in which case the physician may be able to recover the cores. A missing filter member 64 is difficult to detect during a biopsy procedure until the system becomes damaged, potentially resulting in a waste of the biopsy device 100, 200, because seal member 66 around filter can 62 maintains vacuum in the system during operation.

Figure 8:
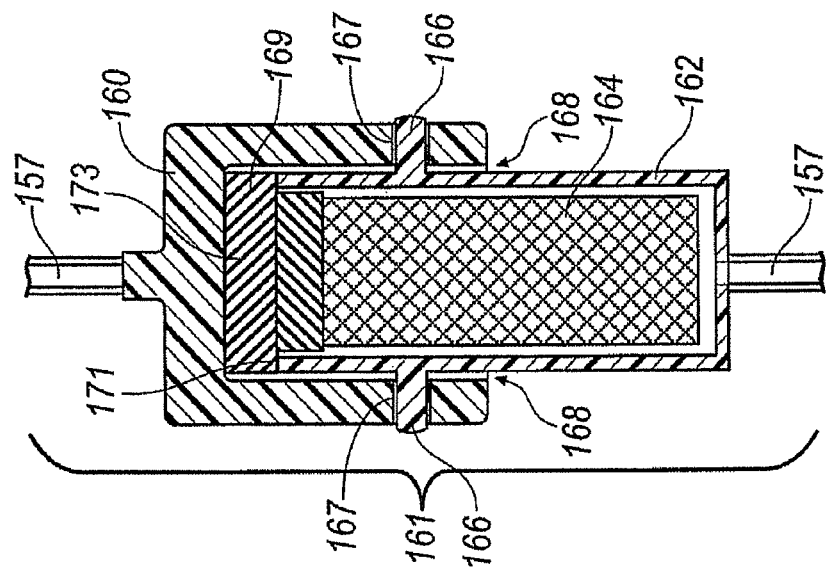
FIG. 8 is a cross-sectional view of a first embodiment of a tissue collection assembly.

Referring now to FIGS. 8-9, embodiments to provide an indicator to a user of a missing filter member will now be discussed. In FIG. 8, a first embodiment of a tissue collection assembly 161 is shown. Tissue collection assembly 161 comprises a cap member 160, a filter can 162, and a filter member 164. In one embodiment, as seen in FIG. 1A, cap member 160 is attached to vacuum line 157. However, it is understood that cap member may be connected directly to a proximal end of a biopsy device. Cap member 228 shown in FIG. 1B is an example of such a configuration.

Filter member 164 is configured with a generally porous material so that fluids may pass through, while tissue cores are retained therein. Filter member 164 is removably positioned within filter can 162, which is configured to be generally hollow. Filter can 162 is received within an open end 168 of cap member 160 and secured to cap member 160 so as to selectively lock filter can 162 to cap member 160. In one particular arrangement, filter can 162 is configured with bayonet mounts 166 that engage mounting channels 167 formed in cap member 160 (see also FIG. 1A, for example). Unlike the prior art tissue collection assemblies, a top portion of filter member 164 is configured with an integral sealing gasket 169. Sealing gasket 169 is configured to be at least as large as the open end of filter can 162 such that sealing gasket 169 cannot be disposed within filter can 162. When filter member 164 is seated within filter can 162, and filter can 162 is connected to cap member 160, sealing gasket 169 is compressed between an outer periphery 171 of the open end of filter can 162 and an interior surface of cap member 160. This compression forms a fluid-tight seal, so as to maintain vacuum through in the biopsy device 100, 200 and to permit tissue cores to be continuously draw into the tissue collection assembly 161. However, unlike the prior art tissue collection assemblies, if filter member 164 is omitted from tissue collection assembly 161, no seal will be created, and a significant vacuum leak will be created. A sensor positioned so as to be in communication with vacuum line 157 will send a signal if the vacuum level drops below a predetermined threshold. Such a vacuum leak will trigger an indicator in the control console 194 (audible, visual or both) to alert that user of a problem and to check the system before tissue cores are taken.

Figure 9A:
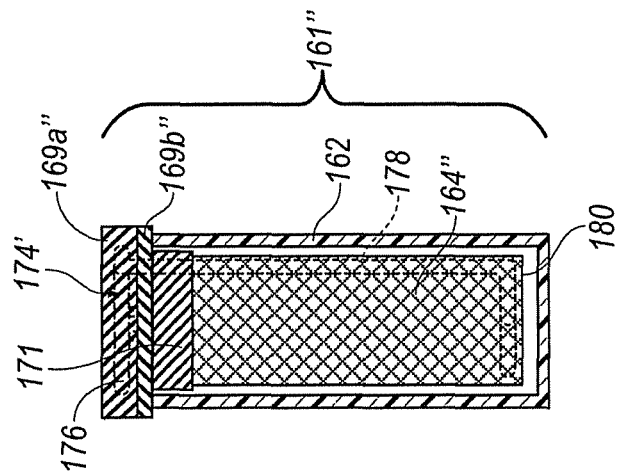
FIG. 9A is a cross-sectional view of a filter can disconnected from a cap member, with a filter member disposed therein.
Figure 9B:
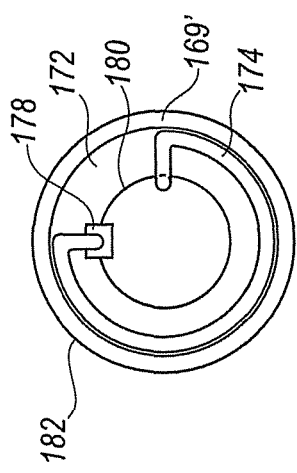
FIG. 9B is a top plan view of the filter can and a scoop of FIG. 8A, with a gasket and the filter member removed for clarity.

FIGS. 9A and 9B illustrate an alternative embodiment of a tissue collection assembly 161'. Tissue collection assembly 161' comprises a filter member 164' disposed within filter can 162 and cap member 160. Cap member 160 has been omitted from FIGS. 9A-9B for clarity. In this embodiment, filter member 164' also includes a sealing gasket 169.' However, sealing gasket 169' is recessed to form an interior mounting flange 172. A scoop member 174 is disposed within filter member 164'. Scoop member 174 includes an upper ring member 176 connected to a body member 178 (shown in phantom). Body member 178 is attached to a foot member 180. In one embodiment, foot member 180 is configured as a non-porous member (as seen in FIG. 9B) that substantially blocks a bottom surface 181 of filter member 164'. In another embodiment, foot member 180 may be configured with small openings (not shown) sized to be smaller than tissue cores taken by biopsy device 100, 200, but permitted fluid to pass through. While foot member 180 is shown as being generally planar, foot member 180 may also be configured with a concave shape (not shown) similar to a ladle. Foot member 180 is sized to fit within an interior of filter member 164', while upper ring member 176 is sized to be at least slightly larger than the open end of filter can 162 such that ring member 176 cannot be disposed within filter member 164'. However, ring member 176 is also sized to be as least slightly larger than an opening formed through the sealing gasket 169' such that ring member 176 may be positioned on mounting flange 172. Body member 178 is configured to have a length that places ring member 176 below a top surface 182 of sealing gasket 169', but also places foot member within filter member 164'.

In operation, filter member 164' is seated within filter can 162 and scoop member 174 is positioned within filter member 164'. Once filter member 164' and scoop member 174 are properly seated within filter can 162, filter can 162 is then connected to cap member 160. When connected, sealing gasket 169' becomes compressed between outer periphery 171 of the open end of filter can 162 and an interior surface of cap member 160 (shown in FIG. 8). This compression forms a fluid-tight seal, so as to maintain vacuum through in the biopsy device 100, 200 and to permit tissue cores to be continuously draw into the tissue collection assembly 161'. However, unlike the prior art tissue collection assemblies, if filter member 164' is omitted from tissue collection assembly 161', no seal will be created, causing a significant vacuum leak. A sensor positioned so as to be in communication with vacuum line 157 will send a signal if the vacuum level drops below a predetermined threshold. Such a vacuum leak will trigger an indicator in the control console 194 (audible, visual or both) to alert that user of a problem and to check the system before tissue cores are taken.

Figure 9C:
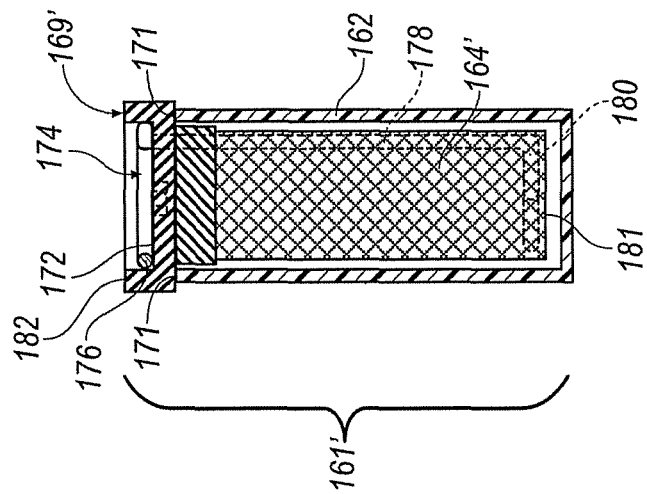
FIG. 9C is a cross-sectional view of an alternative embodiment of a filter can and filter member disconnected from a cap member.

FIG. 9C is yet another embodiment of a tissue collection assembly 161". Tissue collection assembly 161" comprises a filter member 164" disposed within filter can 162 and cap member 160. Cap member 160 has been omitted from FIG. 9C for clarity. In this embodiment, filter member 164" also includes a sealing gasket 169*b*." A scoop member 174' is disposed within filter member 164". Scoop member 174 includes an upper ring member 176 connected to a body member 178 (shown in phantom). Body member 178 is attached to a foot member 180. As described above, foot member 180 may be configured as a non-porous member (as seen in FIG. 9B) that substantially blocks a bottom surface 181 of filter member 164". Alternatively, foot member 180 may be configured with small openings (not shown) sized to be smaller than tissue cores taken by biopsy device 100, 200, but permitted fluid to pass through. In addition, while foot member 180 is shown as being generally planar, foot member 180 may also be configured with a concave shape (not shown). Foot member 180 is sized to fit within an interior of filter member 164". Upper ring member 176 is embedded in a second gasket member 169a". When scoop member 174' is seated in filter member 164" as shown in FIG. 9C, second gasket member 169a" mates with first gasket member 169b". In one embodiment, first and second gasket members 169a", 169b" may be configured with cooperating connection members (not shown), such as a tongue and groove arrangement, to properly mate first and second gasket members 169a", 169b" together.

In the configuration of FIG. 9C, when scoop member 174' and filter member 164" are properly seated within filter can 162, and filter can 162 is secured to cap member 160, first and second gasket members 169a" and 169b" cooperate with the interior surface of cap member 160 to create a seal. If either filter member 164" or scoop member 147' are omitted from filter can 162, no seal will be created, causing a significant vacuum leak. A sensor positioned so as to be in communication with vacuum line 157 will send a signal if the vacuum level drops below a predetermined threshold. Such a vacuum leak will trigger an indicator in the control console 194 (audible, visual or both) to alert that user of a problem and to check the system before tissue cores are taken.

While filter members 164, 164' and 164" are illustrated as being formed as a continuous cylinder member, in yet another embodiment, filter members 164, 164' and 164" may be configured as a selectively openable tissue filter, as shown in described in co-pending U.S. application Ser. No. 11/132,034, the contents of which are incorporated by reference in its entirety. In such embodiments, filter members 164, 164' and 164" include a hinge portion that permits filter members 164, 164' and 164" to be opened along its length to access tissue cores.

Figures 10B, 10C:
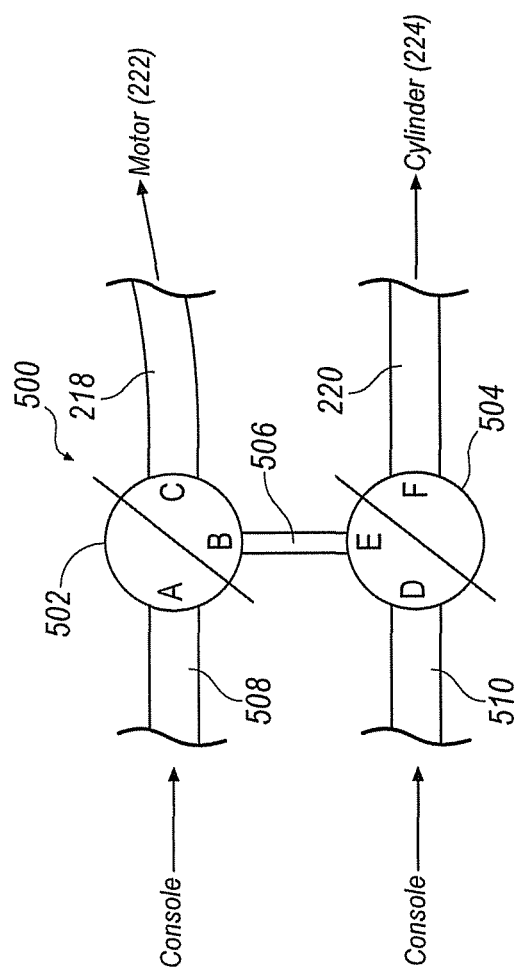
FIG. 10B is an enlarged view of area 9B in FIG. 9A.
FIG. 10C is a chart illustrating different configurations of remote mode toggle system of FIG. 9B.

Turning now to FIGS. 10A-10C, an embodiment of a remote toggle switch assembly 500 will now be described. While remote toggle switch assembly 500 is shown used with handheld surgical device 200, it is understood that remote toggle switch assembly 500 may also be used with surgical device 100.

As described above, surgical device 200 is connected to control console 194. More specifically, saline line 216, motor line 218, biopsy line 220, and vacuum line 226 are all operatively connected to control console 194. Control console 194 is operable between several different operational modes, including a biopsy mode and a lavage mode. A separate actuation mechanism, 195 (such as a foot pedal, for example) selectively supplies power to biopsy device 200.

However, when the biopsy system is used in connection with certain imaging modalities, such as MRI, control console 194 must be placed outside of the surgical suite, away from the patient. Thus, to switch between a biopsy mode and a lavage mode, for example, the user must walk out of the surgical suite to switch the device between modes, leaving the patient's side during a high stress period, and extending the length of the procedure.

To address this issue, remote toggle switch assembly 500 is provided near or actually on biopsy device 200. If located near biopsy device 200, it should be within reach of a user performing the biopsy procedure. Remote toggle switch assembly 500 permits a user to selectively switch to a lavage operation to lavage the biopsy cavity intermittently, or as desired, during a biopsy procedure. More specifically, remote valve switch assembly 500 permits a user to selectively switch to a lavage operation, while control console 194 is still in the biopsy mode, thereby eliminating the need to leave the patient's side.

Remote toggle switch assembly 500 comprises a pair of three-way valves 502, 504 and a connector tube 506, as best seen in FIG. 10B. First three-way valve 502 is positioned between control console 194 and motor line 222 and may be selectively turned to open and close a pathway between control console 194 and motor line 218, as will be explained in further detail below. In addition, first three-valve 502 is also connected to connector tube 506.

Second three-way valve 504 is positioned between control console 194 and biopsy line 220. Like first three-way valve 502, second three-way valve 504 may be selectively turned to open and close a pathway between control console 194 and biopsy line 220. In addition, second three-way valve 504 is also connected to connector tube 506.

Referring now to FIGS. 10B and 10C, operation of remote toggle switch assembly 500 will be explained. As shown in FIG. 10B, first three-way valve 502 is shown as having three separate pathways defined as A, B, and C. Similarly, second three-way valve 504 is shown as having three separate pathways defined as D, E, and F. FIG. 10C illustrates the various configurations of pathways A, B, C, D, E, and F during different operations of biopsy device 200.

When control console 194 is placed in the biopsy mode, both motor line 218 and biopsy line 220 are active. Accordingly, if it is desired to proceed with taking tissue cores in the biopsy mode, first three-way valve member 502 opens pathways A and C, but closes pathway B. Similarly, second three-way valve member 504 opens pathways D and F, but closes pathway E. In this configuration, a tubing line 508 from control console 194 to motor line 218 is fluidly connected. Similarly, a tubing line 510 from control console 194 to biopsy line 220 is also fluidly connected. However, connector line 506 between first and second three-way valve members 502 and 504 is closed.

When it is desired to switch to a lavage operation without changing the operational mode or control console 194, in a first lavage step, pathways A and E are closed, while pathways B, C, D and F remain open. This is the first step of the lavage process and is a venting operation that effectively cuts off air flow to cylinder 224 and motor 222. Further, because control console is still in the biopsy mode, once pathways A and E are closed, and actuation mechanism 195 is depressed, cylinder 224 is vented, such that it retracts. This procedure effectively bypasses control console alarm systems and tricks control console 194 that biopsy device 200 is still operating in the biopsy mode. As such, cutting element 202 is opened.

Once cylinder 224 is vented, during the second lavage step, pathways A and E are opened, and pathways B and F are closed. In this configuration, saline is delivered through saline line 216, and the saline flush is maximized, thereby having biopsy device 200 actively lavaging the biopsy cavity. In addition, vacuum line 226 is pulling vacuum through biopsy device 200. However, control console 194 still remains within the biopsy mode.

Figure 11:
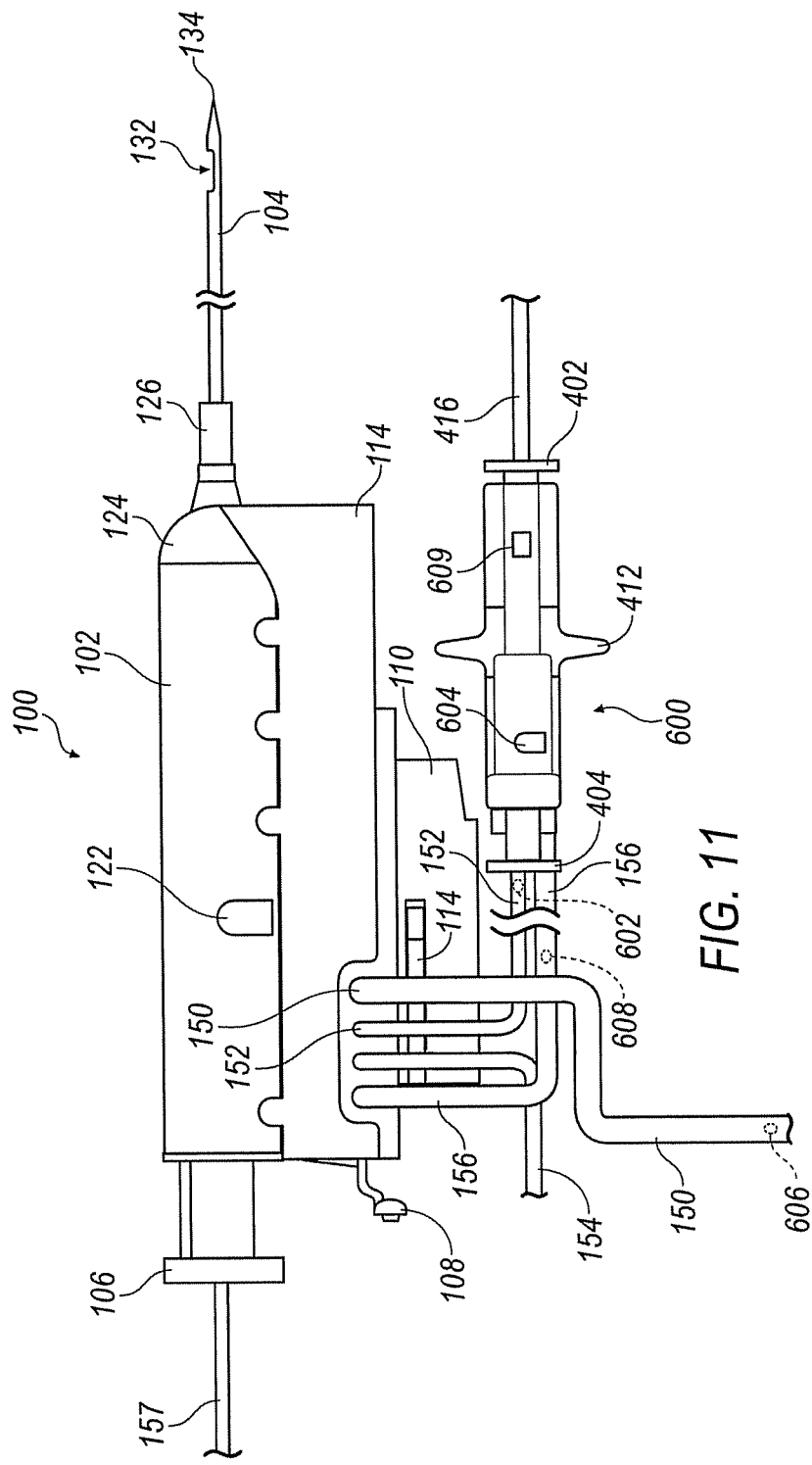
FIG. 11 is an illustration of an error signal system.

Referring now to FIG. 11, an error indicator system 600 for use with biopsy device 100 will now be described. Control console 194 generally offers five modes of operation: set-up, test, manual aspiration, biopsy mode and lavage mode. When control console 194 is in the biopsy mode and a user wants to cock biopsy device 100 or place remote valve 400 in a pre-fired position, a user presses the remote valve button 402 and is able to cock biopsy device 100 or place in a pre-fired position.

When control console 194 is placed in the lavage mode, set-up, or manual aspiration mode, biopsy device 100 will not "cock," when remote valve 400 is placed in a pre-firing position. This is because biopsy device 100 requires pressure from control console 194 to cock biopsy device 100 and this pressure is only available in the biopsy mode. Thus, if a user wants to cock the biops device 100 or put biopsy device in a pre-fired position, biopsy device needs to be placed in the biopsy mode. However, because the distal end of biopsy device 100 is positioned inside the patient (as well as being hidden by the introducer cannula), a user cannot see the biopsy needle and may not notice that biopsy device 100 is in the lavage mode and that cutting element 132 is open. Further, ambient noise within the surgical suite may also serve to mask audible operational indicators of the biopsy device, such that a user may be unable to determine why biopsy device 100 is not operating in the desired manner.

To address this issue, error indicator system 600 incorporates a sensor 602 (shown in phantom) that is disposed in a front chamber of firing line 152. When sensor 602 detects pressure within firing line 152 of at least 28 psi, sensor 602 sends a signal that biopsy device 100 is properly pressurized and is in the correct operational mode for firing the biopsy needle. More specifically, sensor 602 is operatively connected to an indicator 604, in any suitable way, such that the signal triggers indicator 604 to inform the user that biopsy device 100 is cocked or in a "pre-fire" position. Indicator 604 may be a visual indicator, such as an LED light that illuminates when sensor 602 sends a signal that biopsy device 100 is properly pressurized. In addition, or alternatively, indicator 604 may be configured as an audible signal to alert a user that the console needs to be placed in the biopsy mode when a position indicator 609 for remote valve 400 indicates that the remote valve 400 is in the pre-fired position and sensor 602 indicates that firing line 152 is not pressurized.

However, if sensor 602 detects a pressure of less than 28 psi, then indicator 604 will also inform the user that biopsy device 100 is not in the pre-fired position, such that it will prompt the user to insure that the correct operational mode is selected on control console 194. In one example, indicator 604 may be provided with red and green indicator LEDs such that when biopsy device 100 is properly pressurized, the green LED is illuminated to indicate the pre-fired position status. If biopsy device 100 is not in the proper operational mode and sensor 602 indicates a pressure less than 28 psi, then a signal is sent to illuminate the red indicator LED to alter the user to check the control console, which may further alert the user to place control console 194 in the biopsy mode.

Figure 12:
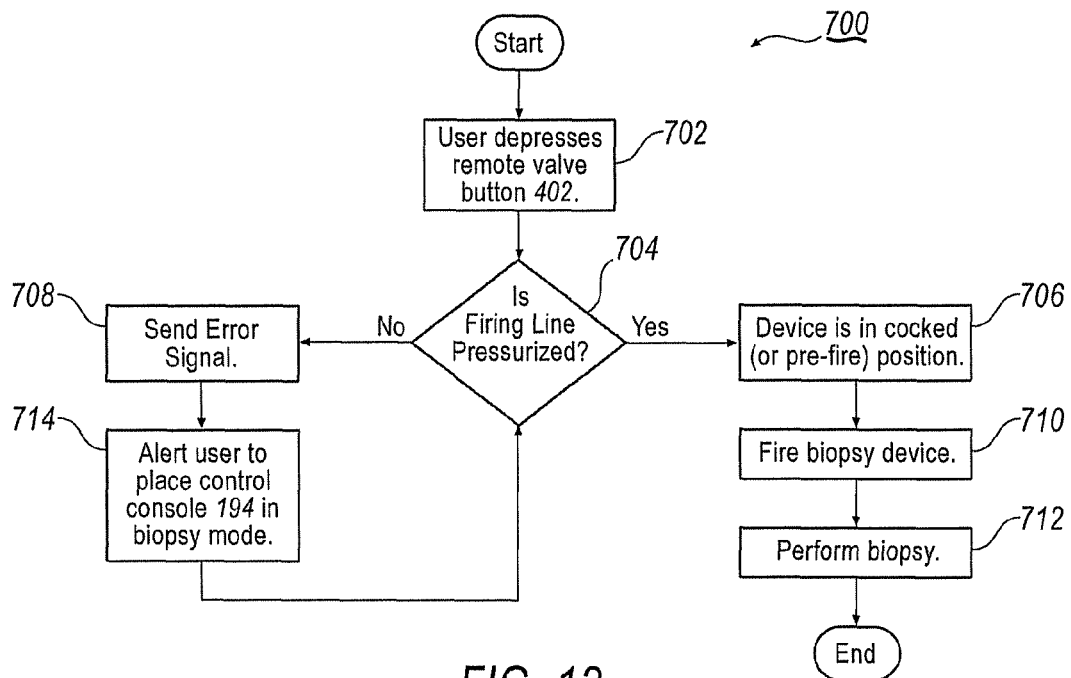
FIG. 12 is a flow chart depicting the operation of an embodiment of the error signal system.

FIG. 12 illustrates a general process flow 700 of error indicator system 600 described above, after biopsy device 100 is powered on. At step 702, the user depresses remote valve button 402. The process then continues to step 704.

At step 704, sensor 602 detects if firing line 152 is pressurized to at least 28 psi. If firing line 152 is pressurized, then the process proceeds to step 706. If firing line 152 is not adequately pressurized, then the process proceeds to step 708. As described above, the pressurized status of firing line 152 indicates which mode control console 194 is in. More specifically, if firing line 152 is pressurized to at least 28 psi, then control console 194 is in the biopsy mode. In contrast, if pressure reading of firing line 152 is 0 psi, then control console 194 is in the lavage mode.

At step 706, biopsy device 100 is in the cocked (or pre-fired) position. In one particular embodiment, remote valve 400 is provided with position indicator 609 which indicates, that biopsy device 100 is in the cocked (or pre-fired) position.

The process then proceeds to step 710. At step 710, biopsy device 100 is fired. The process then proceeds to step 712.

At step 712, the biopsy process is performed. Biopsy cores are severed and pulled through the system to collection canister 161 by the aspiration vacuum. After sampling is complete, tissue cores may be removed from collection canister 161 for further evaluation. The process then ends.

As stated above, returning back to step 704, if sensor 602 detects that firing line 152 is not pressurized, then the process moves to step 708. At step 708, an error signal is sent to the user to indicate that control console 194 is not in the proper mode. The process then proceeds to step 714.

At step 714, the error signal triggers an alert mechanism that informs the user that control console 194 is in the wrong mode. In one exemplary embodiment, control console 194 may be configured to alert the user to place control console 194 into the biopsy mode. The process then returns to step 704.

In one particular embodiment, indicator 604 is disposed on remote valve 400 such that it will be easily visible to a user, even if control console 194 is positioned remotely from the surgical suite. However, it is understood that indicator 604 may also be placed biopsy device 100 itself, on control console 194 or a combination thereof. If an indicator is placed on the control console 194, a separate failure specific message may be triggered, as well. For this particular example, a "select biopsy mode" message may be sent if a user is attempting to cock the device while biopsy device 100 is in the lavage mode.

In one embodiment, sensor 602 is placed in reusable firing line 152*b* (described in connection with FIGS. 4-6). Using sensor 602 with reusable firing line 152*b* reduces costs, as sensor 602 will not be discarded with biopsy device 100 after use.

When a user wants to biopsy, biopsy device 100 is in either a pre-fired position or a fired position. In the fired position, a user actuates biopsy device 100, by, for example, depressing a foot pedal, which causes biopsy device 100 to take tissue cores. However, when biopsy device 100 is in the pre-fired position, and remote valve 400 has not been fired, biopsy device 100 will be unable to acquire tissue cores when operated. In this mode, cutting element 132 is closed (an inner cutting cannula is forward within the outer cannula), but the biopsy cycle will run without triggering an error. Thus, biopsy device 100 will sound like it is performing a normal biopsy cycle, but no tissue cores will be acquired because cutting element 132 remains closed during the cutting cycle. Such a situation may result in discarding a functional device, thereby causing undue waste, or extending the procedure.

To address this issue, in addition to sensor 602 in the front chamber line of firing line 152, error indicator system 600 further includes a sensor 606 disposed in motor line 150. With this arrangement, if both firing and motor lines 152 and 150 are pressurized (i.e., at least 28 psi), then sensors 602 and 606 signal a failure. Sensors 602 and 606 may utilize pneumatic or electronic logic to send the failure signal. The error message will alert the user that they may need to fire biopsy device 100 before proceeding.

As discussed above, sensor 602, as well as sensor 606, are operatively connected to an indicator 604 such that signals trigger indicator 604 to inform the user that biopsy device 100 is function properly or improperly. In one example, indicator 604 may be provided with red and green indicator LEDs such that when biopsy device 100 is properly pressurized, i.e., motor line 150 is pressurized, but firing line 152 is not pressurized, then the green LED is illuminated to indicate that biopsy device 100 is in the "biopsy ready" or "biopsy" mode.

If, however, both motor line 150 and firing line 152 are pressurized, then a signal is sent to illuminate the red indicator LED to alert the user to check to see if remote valve 400 is improperly in the cocked position.

In one particular embodiment, indicator 604 is disposed on remote valve 400 such that it will be easily visible to a user, even if control console 194 is positioned remotely from the surgical suite. However, it is understood that indicator 604 may also be placed biopsy device 100 itself, on control console 194 or a combination thereof. If an indicator is placed on the control console 194, a separate failure specific message may be triggered, as well. For this particular example, a "remote valve 400 is cocked" message may be sent if a user is attempting to take tissue cores while remote valve is cocked.

In one embodiment, sensors 602 and 606 are placed in reusable firing line 152b and reusable motor line 150b (described in connection with FIGS. 4-5). Using sensors 602 and 606 with reusable firing line 152b and reusable motor line 150b reduces costs, as sensors 602 and 606 will not be discarded with biopsy device 100 after use.

Figure 13:
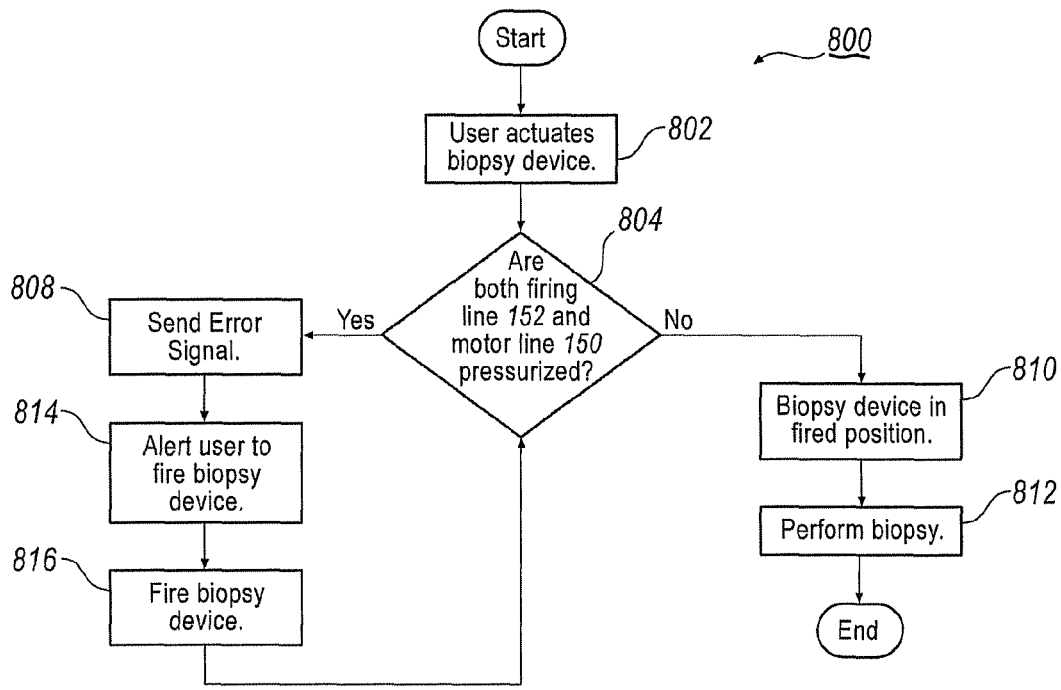
FIG. 13 is a flow chart depicting the operation of another embodiment of the error signal system.

FIG. 13 illustrates a general process flow 800 of error indicator system 600 used to detect if biopsy device 100 is in a fired position or a pre-fired position, after biopsy device 100 is powered on. At step 802, the user actuates biopsy device 100, such as, for example, depressing a foot pedal. The process then continues to step 804.

At step 804, sensors 602 and 606 detects if both firing line 152 and motor line 150 are pressurized to at least 28 psi. If both firing line 152 and motor line 150 are not pressurized, then the process proceeds to step 810. If firing line 152 and motor line 150 are both pressurized, the process proceeds to step 808.

At step 810 the signal from sensor 602 determines that biopsy device 100 is in the fired position. The process then proceeds to step 812 whereby the user performs the biopsy operation. The process then ends.

Returning back to step 804, as stated above, if both firing line 152 and motor line 150 are pressurized, then an error signal is sent at step 808. The process then proceeds to step 814.

At step 814, the error signal triggers an alert mechanism that informs the user to fire biopsy device 100. The process then proceeds to step 816. At step 816 a user fires the biopsy device 100. The process then returns to step 804.

Another issue that may occur during operation of biopsy device 100, is that a user may accidentally place remote valve 400 between the cocked and fired position, whereby the inner cannula is retracted, but outer cannula 131 is fired forward. In such a position, remote valve 400 will only be partially cocked. As such, when a user actuates biopsy device 100 (such as by depressing a foot pedal), the aperture 132 remains open and does not close to cut tissue properly. Indeed, no samples, or only bits of tissue cores will be obtained, such that biopsy device 100 will not function properly.

To address this situation, in addition to sensor 606 in motor line 150, a sensor 608 is also placed in pressure line 156, which is connected between remote valve 400 and biopsy device 100. Using pneumatic or electronic control logic, sensor 606 detects if motor line 150 is properly pressurized and sensor 608 detects if pressure line 156 is pressurized. During the biopsy cycle, motor line 150 is pressurized for approximately 3 seconds. If 28 psi is not detected in line 156 by sensor 608, then a failure signal is sent because this would indicate that the motor is not advancing during the biopsy cycle. A user may be prompted to fire biopsy device completely (i.e., by depressing remote valve 400 completely) prior to proceeding with biopsy operation.

Like the embodiments described above, the signals sent by sensors 606 and 608 may be operatively connected to an indicator 604. Indicator 604 may be placed on remote valve 400, biopsy device 100 or control console 194.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

The invention claimed is:

1. A tissue filter assembly for collecting tissue excised by a tissue cutting device, comprising:
   a cap defining a tissue inlet port configured to be attached to a tissue aspiration line;
   a filter can having an open end configured for removable attachment to the cap;
   a porous filter trap sized to be removably seated in the filter can and configured for retaining excised tissue passing through the tissue inlet port, the filter trap defining a tissue collection chamber, the filter can defining a vacuum access port in fluid communication with the tissue collection chamber, the vacuum access port configured to be attached to a vacuum line, such that, when a tissue aspiration line is attached to the inlet port, the cap is attached to the filter can, and the vacuum line is attached to the vacuum access port, the respective tissue aspiration line, tissue collection chamber and vacuum line are in fluid communication with each other; and
   a gasket configured to be compressed between the cap and an outer peripheral wall of the filter can,
   wherein the cap, gasket, and filter can are collectively configured (i) to form a vacuum-tight seal when the cap is attached to the filter can if the filter trap is seated in the filter can, and (ii) to not form a vacuum-tight seal when the cap is attached to the filter can if the filter trap is not seated in the filter can.

2. The tissue filter assembly of claim 1, further comprising a sensor positioned so as to be in fluid communication with the vacuum line when the vacuum line is attached to the vacuum access port, wherein the sensor is configured to send a signal if a vacuum level drops below a predetermined threshold.

3. The tissue filter assembly of claim 1, further comprising a scoop member sized to be disposed within the filter trap when the filter trap is seated in the filter can and the filter can is attached to the cap, the scoop member comprising an upper ring member connected to a body member, and a foot member attached to the body member.

4. The tissue filter assembly of claim 3, the gasket having a recessed section that forms an interior mounting flange, such that the upper ring member of the scoop member is seated on the interior mounting flange when the scoop member is disposed within the filter trap.

5. The tissue filter assembly of claim 4, wherein the gasket is integrally formed with the filter can.

6. The tissue filter assembly of claim 1, wherein the cap and filter can comprise a bayonet mount for removable attachment to each other.

7. The tissue filter assembly of claim 1, wherein the gasket is integrally formed with the filter can.

8. A tissue filter assembly for collecting tissue excised by a tissue cutting device, the filter assembly comprising:
   a cap defining a tissue inlet port configured to be attached to a tissue aspiration line;
   a filter can having an open end, wherein the cap and the filter can comprise a bayonet mount for removable attachment to each other;
   a porous filter trap sized to be removably seated in the filter can, the filter trap defining a tissue collection chamber configured for retaining excised tissue passing through the tissue inlet port, the filter can defining a vacuum access port configured for removable attachment to a flexible tubing vacuum line, such that, when the tissue aspiration line is attached to the tissue inlet port, the cap is attached to the filter can, and the vacuum line is attached to the vacuum access port, the respective aspiration line, tissue collection chamber and vacuum line are in fluid communication with each other; and
   a gasket disposed around the open end of the filter can, the gasket configured to be compressed between the cap and the filter can to create a vacuum-tight seal when the filter trap is seated within the filter can and the cap is attached to the filter can, wherein the filter can and the cap are configured to not form a vacuum-tight seal without the filter trap being seated in the filter can.

9. The tissue filter assembly of claim 8, further comprising a sensor positioned so as to be in fluid communication with the vacuum line when the vacuum line is attached to the vacuum access port, wherein the sensor is configured to send a signal if a vacuum level drops below a predetermined threshold.

10. The tissue filter assembly of claim 8, further comprising a scoop member sized to be disposed within the filter trap when the filter trap is seated in the filter can and the filter can is attached to the cap, the scoop member comprising an upper ring member connected to a body member, and a foot member attached to the body member.

11. The tissue filter assembly of claim 10, the gasket comprising a recessed section that forms an interior mounting flange, such that the upper ring member of the scoop member is seated on the interior mounting flange when the scoop member is disposed within the filter trap.

12. The tissue filter assembly of claim 8, wherein the gasket is integrally formed with the filter can.

* * * * *